United States Patent
Harr et al.

(10) Patent No.: US 9,699,816 B2
(45) Date of Patent: Jul. 4, 2017

(54) DOCKING STATION FOR AN ENTERAL FEEDING PUMP

(71) Applicant: Covidien LP, Mansfield, MA (US)

(72) Inventors: James M. Harr, Wentzville, MO (US); Gabriel McHugh, Braintree, MA (US); Lester Paul Trelford, St. Louis, MO (US); Gary J. Waldhoff, St. Charles, MO (US); Dennis Scott Prows, Lutz, FL (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/152,131

(22) PCT Filed: Sep. 13, 2013

(86) PCT No.: PCT/US2013/059703
§ 371 (c)(1),
(2) Date: Jan. 10, 2014

(87) PCT Pub. No.: WO2014/043499
PCT Pub. Date: Mar. 20, 2014

(65) Prior Publication Data
US 2015/0305073 A1 Oct. 22, 2015

Related U.S. Application Data

(60) Provisional application No. 61/700,682, filed on Sep. 13, 2012.

(51) Int. Cl.
*H02J 1/00* (2006.01)
*H04W 76/02* (2009.01)
(Continued)

(52) U.S. Cl.
CPC ...... *H04W 76/023* (2013.01); *G06F 19/3418* (2013.01); *H02J 7/0052* (2013.01);
(Continued)

(58) Field of Classification Search
CPC ............... H04W 76/023; A61M 2202/0482
See application file for complete search history.

(56) References Cited

U.S. PATENT DOCUMENTS

| 5,451,839 | A | 9/1995 | Rappaport et al. |
| 5,655,897 | A | 8/1997 | Neftel et al. |

(Continued)

FOREIGN PATENT DOCUMENTS

| CA | 2 644 695 | 1/2004 |
| CA | 2 648 885 | 11/2007 |

(Continued)

OTHER PUBLICATIONS

Response filed Feb. 18, 2014 for Office Action dated Sep. 27, 2013 for U.S. Appl. No. 13/241,620; 24 pages.

(Continued)

*Primary Examiner* — Daniel Cavallari
(74) *Attorney, Agent, or Firm* — Blaine A. Page, Esq.

(57) ABSTRACT

Described herein are concepts, systems, circuits and techniques for a docking station configured to couple to an enteral feeding pump or other medical device. In one embodiment, the docking station includes a wireless transmitter for communicating data, such as operating parameters and/or status, to a remote monitor over a wireless communication link, to permit remote monitoring of certain pump diagnostics. In some embodiments, the docking station may utilize the wireless communication link to permit control and/or data exchange with the feeding pump. This may be in addition to or in place of the remote monitoring. The pump may also contain a receiver for receiving data such as operating parameter instructions, general operating instructions, and/or commands.

13 Claims, 15 Drawing Sheets

(51) Int. Cl.
*G06F 19/00* (2011.01)
*H02J 7/00* (2006.01)
*H02J 7/02* (2016.01)
*H04B 7/14* (2006.01)
*H04W 4/00* (2009.01)

(52) U.S. Cl.
CPC ............ *H02J 7/025* (2013.01); *H04B 7/14* (2013.01); *H04W 4/008* (2013.01); *A61M 2202/0482* (2013.01)

(56) References Cited

U.S. PATENT DOCUMENTS

| | | |
|---|---|---|
| 5,936,539 A | 8/1999 | Fuchs |
| 6,062,829 A | 5/2000 | Ognier |
| 6,221,012 B1 | 4/2001 | Maschke et al. |
| 6,377,162 B1 | 4/2002 | Delestienne et al. |
| 6,377,806 B1 | 4/2002 | Tokyuoshi |
| 6,442,433 B1 | 8/2002 | Linberg |
| 6,519,569 B1 | 2/2003 | White et al. |
| 6,578,002 B1 | 6/2003 | Derzay et al. |
| 6,695,806 B2 | 2/2004 | Gelfand et al. |
| 6,790,198 B1 | 9/2004 | White et al. |
| 6,839,753 B2 | 1/2005 | Biondi et al. |
| 6,942,473 B2 | 9/2005 | Abrahamson et al. |
| 7,028,182 B1 | 4/2006 | Killcommons |
| 7,050,984 B1 | 5/2006 | Kerpelman et al. |
| 7,082,460 B2 | 7/2006 | Hansen et al. |
| D535,202 S | 1/2007 | Sisk et al. |
| 7,178,149 B2 | 2/2007 | Hansen |
| 7,185,014 B1 | 2/2007 | Hansen |
| 7,236,936 B2 | 6/2007 | White et al. |
| 7,294,105 B1 | 11/2007 | Islam |
| 7,316,648 B2 | 1/2008 | Kelly |
| 7,349,947 B1 | 3/2008 | Slage et al. |
| 7,508,787 B2 | 3/2009 | Doshi et al. |
| 7,529,561 B2 | 5/2009 | Heinonen et al. |
| 7,539,532 B2 | 5/2009 | Tran |
| 7,539,533 B2 | 5/2009 | Tran |
| 7,558,622 B2 | 7/2009 | Tran |
| 7,613,169 B2 | 11/2009 | Vaittinen et al. |
| 7,645,258 B2 | 1/2010 | White et al. |
| 7,707,047 B2 | 4/2010 | Hasan et al. |
| 7,733,224 B2 | 6/2010 | Tran |
| 7,749,164 B2 | 7/2010 | Davis |
| 7,752,058 B2 | 7/2010 | Sasaki et al. |
| 7,827,040 B2 | 11/2010 | Brown |
| 7,873,772 B2 | 1/2011 | Waldhoff et al. |
| 7,934,912 B2 | 5/2011 | Voltenburg, Jr. et al. |
| 7,937,370 B2 | 5/2011 | Hansen |
| 7,942,844 B2 | 5/2011 | Moberg et al. |
| 7,949,164 B2 | 5/2011 | Degani et al. |
| 7,949,404 B2 | 5/2011 | Hill |
| 7,978,062 B2 | 7/2011 | LaLonde |
| 8,002,701 B2 | 8/2011 | John et al. |
| RE42,934 E | 11/2011 | Thompson |
| 8,047,819 B2 | 11/2011 | Lawrence et al. |
| 8,073,008 B2 | 12/2011 | Mehta et al. |
| 8,095,381 B2 | 1/2012 | Simmons et al. |
| 8,108,543 B2 | 1/2012 | Hansen |
| 8,125,318 B2 | 2/2012 | Heimbrock et al. |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,126,735 B2 | 2/2012 | Dicks et al. |
| 8,131,564 B2 | 3/2012 | Dicks et al. |
| 8,131,565 B2 | 3/2012 | Dicks et al. |
| 8,131,566 B2 | 3/2012 | Dicks et al. |
| 8,140,356 B2 | 3/2012 | Dicks et al. |
| 8,155,982 B2 | 4/2012 | Dicks et al. |
| 8,197,236 B2 | 6/2012 | McIntosh |
| 8,200,195 B2 | 6/2012 | Le Saint et al. |
| 8,214,549 B2 | 7/2012 | Dicks et al. |
| 8,326,648 B2 | 12/2012 | Kenedy et al. |
| 8,373,556 B2 | 2/2013 | LaLonde et al. |
| 8,395,498 B2 | 3/2013 | Gaskill et al. |
| 8,428,722 B2 | 4/2013 | Verhoef et al. |
| 8,515,547 B2 | 8/2013 | Mass et al. |
| 8,545,198 B2 | 10/2013 | Artsyukhovich et al. |
| 8,587,427 B2 | 11/2013 | LaLonde et al. |
| 8,694,600 B2 | 4/2014 | Gaines et al. |
| 2002/0178126 A1 | 11/2002 | Beck et al. |
| 2002/0198473 A1 | 12/2002 | Kumar et al. |
| 2004/0155772 A1 | 8/2004 | Medema et al. |
| 2004/0204743 A1 | 10/2004 | McGrath et al. |
| 2005/0010093 A1 | 1/2005 | Ford et al. |
| 2005/0185398 A1 | 8/2005 | Scannell, Jr. |
| 2005/0188853 A1 | 9/2005 | Scannell, Jr. |
| 2005/0201300 A1 | 9/2005 | Bridgelall |
| 2005/0243988 A1 | 11/2005 | Barclay et al. |
| 2005/0288571 A1 | 12/2005 | Perkins et al. |
| 2006/0154642 A1 | 7/2006 | Scannell, Jr. |
| 2006/0238333 A1 | 10/2006 | Welch et al. |
| 2007/0106126 A1 | 5/2007 | Mannheimer et al. |
| 2007/0156033 A1 | 7/2007 | Causey, III et al. |
| 2007/0180140 A1 | 8/2007 | Welch et al. |
| 2007/0186923 A1 | 8/2007 | Poutiatine et al. |
| 2007/0216764 A1 | 9/2007 | Kwak |
| 2007/0230197 A1 | 10/2007 | Scannell, Jr. |
| 2007/0253380 A1 | 11/2007 | Jollota et al. |
| 2007/0254593 A1 | 11/2007 | Jollota et al. |
| 2007/0255125 A1 | 11/2007 | Moberg et al. |
| 2007/0255250 A1 | 11/2007 | Moberg et al. |
| 2007/0258395 A1 | 11/2007 | Jollota et al. |
| 2007/0268687 A1 | 11/2007 | Scannell, Jr. |
| 2007/0272670 A1 | 11/2007 | Chen |
| 2007/0276270 A1 | 11/2007 | Tran |
| 2008/0004904 A1 | 1/2008 | Tran |
| 2008/0004907 A1 | 1/2008 | Bayne |
| 2008/0012761 A1 | 1/2008 | Derrick et al. |
| 2008/0071234 A1 | 3/2008 | Kelch et al. |
| 2008/0072900 A1 | 3/2008 | Kenyon et al. |
| 2008/0097550 A1 | 4/2008 | Dicks et al. |
| 2008/0097551 A1 | 4/2008 | Dicks et al. |
| 2008/0097552 A1 | 4/2008 | Dicks et al. |
| 2008/0097793 A1 | 4/2008 | Dicks et al. |
| 2008/0097908 A1 | 4/2008 | Dicks et al. |
| 2008/0097909 A1 | 4/2008 | Dicks et al. |
| 2008/0097910 A1 | 4/2008 | Dicks et al. |
| 2008/0097911 A1 | 4/2008 | Dicks et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0097917 A1 | 4/2008 | Dicks et al. |
| 2008/0108880 A1 | 5/2008 | Young et al. |
| 2008/0183502 A1 | 7/2008 | Dicks et al. |
| 2008/0224852 A1 | 9/2008 | Dicks et al. |
| 2008/0281168 A1 | 11/2008 | Gibson et al. |
| 2009/0019061 A1 | 1/2009 | Scannell, Jr. |
| 2009/0023391 A1 | 1/2009 | Falck |
| 2009/0058635 A1 | 3/2009 | LaLonde et al. |
| 2009/0058636 A1 | 3/2009 | Gaskill et al. |
| 2009/0062887 A1 | 3/2009 | Mass et al. |
| 2009/0063187 A1 | 3/2009 | Johnson et al. |
| 2009/0063193 A1 | 3/2009 | Barton et al. |
| 2009/0073694 A1 | 3/2009 | Scannell, Jr. |
| 2009/0087325 A1 | 4/2009 | Voltenburg, Jr. et al. |
| 2009/0105549 A1 | 4/2009 | Smith et al. |
| 2009/0115628 A1 | 5/2009 | Dicks et al. |
| 2009/0128320 A1 | 5/2009 | Needham et al. |
| 2009/0184835 A1 | 7/2009 | Deaver, Sr. et al. |
| 2009/0203329 A1 | 8/2009 | White et al. |
| 2009/0234672 A1 | 9/2009 | Dicks et al. |
| 2009/0247114 A1 | 10/2009 | Sennett et al. |
| 2009/0252117 A1 | 10/2009 | Sherman et al. |
| 2009/0299788 A1 | 12/2009 | Huber et al. |
| 2009/0306747 A1 | 12/2009 | Fischer et al. |
| 2010/0011000 A1 | 1/2010 | Chakara et al. |
| 2010/0027518 A1 | 2/2010 | Wang |
| 2010/0077115 A1 | 3/2010 | Rofougran |
| 2010/0079276 A1 | 4/2010 | Collins et al. |

(56) References Cited

U.S. PATENT DOCUMENTS

| | | |
|---|---|---|
| 2010/0080200 A1 | 4/2010 | Stewart |
| 2010/0082371 A1 | 4/2010 | Kamp et al. |
| 2010/0085948 A1 | 4/2010 | Yu et al. |
| 2010/0117835 A1 | 5/2010 | Nanikashvili |
| 2010/0138235 A1 | 6/2010 | Marks et al. |
| 2010/0166170 A1 | 7/2010 | East et al. |
| 2010/0198142 A1 | 8/2010 | Sloan et al. |
| 2010/0211713 A1* | 8/2010 | Waldhoff ............ A61B 5/0002 710/303 |
| 2010/0217723 A1 | 8/2010 | Sauerwein, Jr. et al. |
| 2010/0219250 A1 | 9/2010 | Wang |
| 2010/0234695 A1 | 9/2010 | Morris |
| 2010/0260061 A1 | 10/2010 | Bojahra et al. |
| 2010/0279647 A1 | 11/2010 | Jacobs et al. |
| 2010/0292556 A1 | 11/2010 | Golden |
| 2010/0317286 A1 | 12/2010 | Jung et al. |
| 2010/0318578 A1 | 12/2010 | Treu et al. |
| 2011/0021902 A1 | 1/2011 | Kim et al. |
| 2011/0032822 A1 | 2/2011 | Soomro |
| 2011/0066555 A1 | 3/2011 | Dicks et al. |
| 2011/0078441 A1 | 3/2011 | Dicks et al. |
| 2011/0087756 A1 | 4/2011 | Biondi et al. |
| 2011/0093283 A1 | 4/2011 | Dicks et al. |
| 2011/0093284 A1 | 4/2011 | Dicks et al. |
| 2011/0093285 A1 | 4/2011 | Dicks et al. |
| 2011/0093286 A1 | 4/2011 | Dicks et al. |
| 2011/0093287 A1 | 4/2011 | Dicks et al. |
| 2011/0093297 A1 | 4/2011 | Dicks et al. |
| 2011/0148624 A1 | 6/2011 | Eaton et al. |
| 2011/0158430 A1 | 6/2011 | Dicks et al. |
| 2011/0161111 A1 | 6/2011 | Dicks et al. |
| 2011/0179405 A1 | 7/2011 | Dicks et al. |
| 2011/0255454 A1 | 10/2011 | Hauser et al. |
| 2011/0270045 A1 | 11/2011 | Lebel et al. |
| 2011/0273287 A1 | 11/2011 | LaLonde et al. |
| 2011/0280224 A1 | 11/2011 | Falck et al. |
| 2011/0282671 A1 | 11/2011 | Dicks et al. |
| 2011/0292862 A1 | 12/2011 | Shimizu |
| 2012/0004925 A1 | 1/2012 | Braverman et al. |
| 2012/0034117 A1 | 2/2012 | Pfouts et al. |
| 2012/0083735 A1 | 4/2012 | Pfouts |
| 2012/0108917 A1 | 5/2012 | Libbus et al. |
| 2012/0182143 A1* | 7/2012 | Gaines ................ A61B 5/0022 340/539.12 |
| 2012/0182894 A1 | 7/2012 | Gaines et al. |
| 2012/0182924 A1 | 7/2012 | Gaines et al. |
| 2012/0182927 A1 | 7/2012 | Wiesner et al. |
| 2012/0184207 A1 | 7/2012 | Gaines et al. |
| 2012/0184237 A1 | 7/2012 | Gaines et al. |
| 2012/0185268 A1 | 7/2012 | Wiesner et al. |
| 2012/0226768 A1 | 9/2012 | Gaines et al. |
| 2012/0226771 A1 | 9/2012 | Harrington et al. |
| 2012/0256751 A1 | 10/2012 | Nallabelli et al. |
| 2012/0293323 A1 | 11/2012 | Kaib et al. |
| 2013/0015966 A1 | 1/2013 | Soomro et al. |
| 2013/0021169 A1 | 1/2013 | Soomro et al. |
| 2013/0022022 A1 | 1/2013 | Schmitt |
| 2013/0066644 A1 | 3/2013 | Dicks et al. |
| 2013/0071272 A1 | 3/2013 | Juretich et al. |
| 2013/0147622 A1 | 6/2013 | LaLonde et al. |
| 2013/0154851 A1 | 6/2013 | Gaskill et al. |
| 2013/0162426 A1 | 6/2013 | Wiesner et al. |
| 2013/0278414 A1 | 10/2013 | Sprigg et al. |
| 2013/0310896 A1 | 11/2013 | Mass |
| 2014/0009271 A1 | 1/2014 | Collins et al. |
| 2014/0010691 A1 | 1/2014 | Lanigan et al. |
| 2014/0062718 A1 | 3/2014 | LaLonde et al. |
| 2014/0135731 A1 | 5/2014 | Breitweiser et al. |
| 2014/0142979 A1 | 5/2014 | Mitsunaga |
| 2014/0152466 A1 | 6/2014 | Wiesner et al. |

FOREIGN PATENT DOCUMENTS

| | | |
|---|---|---|
| CA | 2 644 635 | 8/2008 |
| CN | 101601040 A | 12/2009 |
| EP | 2 227 063 | 9/2010 |
| JP | 2003109160 | 4/2003 |
| JP | 2006520657 | 9/2006 |
| JP | 2007531442 | 11/2007 |
| JP | 2008108170 | 5/2008 |
| JP | 2009-535715 A | 1/2009 |
| JP | 2010-524050 | 7/2010 |
| JP | 2010-524050 A | 7/2010 |
| JP | 2011-502369 A | 1/2011 |
| KR | 10-2008-0016458 | 2/2008 |
| KR | 10-2009-0122968 | 12/2009 |
| KR | 10-2010-0028318 | 3/2010 |
| WO | WO 94/16617 | 8/1994 |
| WO | WO 98/14228 | 4/1998 |
| WO | WO 03/048919 A1 | 6/2003 |
| WO | WO 2004/070994 A2 | 8/2004 |
| WO | WO 2004/070994 A3 | 8/2004 |
| WO | WO 2004/084720 A2 | 10/2004 |
| WO | WO 2005/057294 A1 | 6/2005 |
| WO | WO 2005/057834 A2 | 6/2005 |
| WO | WO 2005/098736 A2 | 10/2005 |
| WO | WO 2007/124091 A1 | 11/2007 |
| WO | WO 2007/127879 A2 | 11/2007 |
| WO | WO 2008/052034 A1 | 5/2008 |
| WO | WO 2008/097316 A1 | 8/2008 |
| WO | WO 2009/032134 A2 | 3/2009 |
| WO | WO 2009/063303 A1 | 5/2009 |
| WO | WO 2010/085138 A2 | 7/2010 |

OTHER PUBLICATIONS

Response filed Feb. 13, 2014 for Office Action dated Sep. 5, 2013 for U.S. Appl. No. 13/006,769; 18 pages.
Response flied with RCE on Feb. 13, 2014 for Final Office Action dated Dec. 2, 2013 for U.S. Appl. No. 13/006,784; 24 pages.
European Response filed Mar. 3, 2014; to Official Communication dated Aug. 22, 2013; and to the Written Opinion; for European Pat. App. No. 12704944.3; 15 pages.
European Response filed Mar. 3, 2014; to Official Communication dated Aug. 22, 2013; and to the Written Opinion; for European Pat. App. No. 12701584.0; 11 pages.
PCT Search Report and Written Opinion of the ISA dated Mar. 4, 2014; for PCT Pat. App. No. PCT/US2013/059703; 12 pages.
Amendment filed Mar. 26, 2014, to Office Action dated Dec. 27, 2013; for U.S. Appl. No. 13/352,575; 12 pages.
Amendment filed Mar. 26, 2014; to Office Action dated Jan. 7, 2014; for U.S. Appl. No. 13/353,565; 15 pages.
Amendment and Response to Restriction Requirement for Office Action dated Feb. 10, 2014; filed Mar. 21, 2014; for U.S. Appl. No. 13/352,608; 7 pages.
Letter from CCPIT Patent and Trademark Law Office dated Mar. 3, 2014; for Chinese Pat. App. No. 201280011025.0; 1 page.
Chinese Voluntary Amendment (including English translation) received Mar. 3, 2014; for Chinese Pat. App. No. 201280011025.0; 16 pages.
Notice of Allowance dated Apr. 30, 2014; for U.S. Appl. No. 13/241,620; 21 pages.
Office Acton dated Apr. 29, 2014; for U.S. Appl. No. 13/352,608; 50 pages.
Mexican Official Action recieved May 2, 2014, for Mexican Pat. App. No. MX/A2013/008157; 3 pages.
Office Action dated May 27, 2014; for U.S. Appl. No. 13/334,463; 48 pages.
Mexican Notice of Allowance dated May 7, 2014; for Mexican Pat. App. No. MX/a/2013/009985; 2 pages.
Mexican Office Action received Apr. 22, 2014; for Mexican Pat. App. No. MX/a/2013/008154; 4 pages.
Response to Office Action dated Apr. 29, 2014 for U.S. Appl. No. 13/352,608, filed Jan. 18, 2014.
Notice of Allowance dated Jun. 6, 2014 for U.S. Appl. No. 14/154,285, filed Jan. 14, 2014.

(56) References Cited

OTHER PUBLICATIONS

Notice of Allowance dated Jun. 9, 2014 for U.S. Appl. No. 13/006,769, filed Jan. 14, 2011.
Office Action dated Jun. 16, 2014 for U.S. Appl. No. 13/353,565, filed Jan. 19, 2012.
Japanese Office Action dated May 30, 2014 for Application No. 2013-549531.
Notice of Allowance for U.S. Appl. No. 13/352,575, filed Jan. 18, 2012.
Office Action dated Jun. 20, 2014 for U.S. Appl. No. 13/334,447, filed Dec. 22, 2011.
European Search Report dated Jun. 14, 2014; for European Patent Application No. 14168075.1-1951; 8 pages.
Office Action dated Jun. 23, 2014 for U.S. Appl. No. 13/334,459, filed Dec. 22, 2011 44 pages.
U.S. Appl. No. 14/308,881, filed Jun. 19, 2014, Gaines, et al.
Response (and English Language Passage) received Jul. 7, 2014; for Mexican Pat. App. No. MX/a/2013/008154; 16 pages.
U.S. Response to 312 Amendment dated Jul. 21, 2014; for U.S. Appl. No. 14/154,285; 3 pages.
Japanese Office Action (including English translation) dated Jun. 23, 2014; for Japanese Pat. App. No. 2013-549532 6 pages.
PCT International Preliminary Report on Patentability of the ISA dated Jul. 3, 3014; for PCT Pat. App. No. PCT/US2012/068892; 8 pages.
PCT International Preliminary Report on Patentability of the ISA dated Jul. 3, 2014; for PCT Pat. App. No. PCT/US2012/068888; 8 pages.
Singapore Written Opinion dated Jun. 18, 2014; for Singapore Pat. App. No. 2013053236; 11 pages.
Singapore Written Opinion dated Jun. 19, 2014; for Singapore Pat. App. No. 2013065230; 22 pages.
Response with Terminal Disclaimer filed Jul. 30, 2014; to Office Action dated Jun. 20, 2014; for U.S. Appl. No. 13/334,447; 15 pages.
Response with Terminal Disclaimer filed Jul. 30, 2014; to Office Action dated Jun. 23, 2014; for U.S. Appl. No. 13/334,459; 13 pages.
Response filed Aug. 4, 2014; to Office Action dated May 27, 2014; for U.S. Appl. No. 13/334,463; 21 pages.
Response filed Jul. 30, 2014; to Final Office Action dated Jun. 16, 2014; to U.S. Appl. No. 13/353,565; 22 pages.
Mexican Response to Office Action recieved Jul. 29, 2014; for Mexican Pat. App. No. MX/a/2013/008157; 14 pages.
PCT International Preliminary Report on Patentability dated Jul. 3, 2014; for PCT Pat. App. No. PCT/US2012/068895; 10 pages.
Final Office Action dated Aug. 6, 2014; for U.S. Appl. No. 13/352,608; 38 pages.
PCT International Preliminary Report on Patentability of the ISA dated Jul. 31, 2014; for PCT Pat. App. No. PCT/US2013/020069; 6 pages.
PCT International Preliminary Report on Patentability of the ISA dated Jul. 31, 2014; for PCT Pat. App. No. PCT/US2013/020071; 6 pages.
Singapore Written Opinion dated Jul. 25, 2014; for Singapore Pat. App. No. 2013053244; 7 pages.
U.S. Appl. No. 14/462,025, filed Aug. 18, 2014, Wiesner et al.
Notice of Allowance dated Aug. 20, 2014, for U.S. Appl. No. 13/334,447; 25 pages.
Notice of Allowance dated Aug. 15, 2014, for U.S. Appl. No. 13/334,459; 20 pages.
PCT International Preliminary Report on Patentability and Written Opinion of the ISA dated Jul. 31, 2014; for PCT Pat. App. No. PCT/US2013/021530; 8 pages.
Office Action dated Sep. 9, 2014; for U.S. Appl. No. 13/353,565; 24 pages.
Gaines et al. "Improved Wireless Relay Module for Remote Monitoring Systems;" U.S. Appl. No. 14/308,881, filed Jun. 19, 2014; 36 pages.

Canadian Office Action dated Aug. 4, 2014; for Canadian Pat. App. No. 2,823,600; 3 pages.
PCT Search Report and Written Opinion of the ISA dated Apr. 29, 2013; for PCT Pat. App. No. PCT/US2013/021530; 10 pages.
Notice of Allowance dated Sep. 22, 2014; for U.S. Appl. No. 13/006,784; 47 pages.
Mexican Memo Concerning the Official Action dated Sep. 19, 2014; regarding Mexican Office Action for Mexican Patent Application No. MX/A/2013/008157; 1 page.
Japanese Amendment and Argument with Claims and Argument in English dated Sep. 22, 2014; for Japanese Pat. App. No. 2013-549532; 28 pages.
Australian Patent Examination Report No. 1 dated Sep. 1, 2014; for Australian Pat. App. No. 2012205515; 3 pages.
European Search Report dated Sep. 18, 2014; for European Pat. Ap. No. 14167899.5; 9 pages.
Canadian Office Action dated Aug. 8, 2014; for Canadian Pat. App. No. 2,823,700; 7 pages.
Written Opinion dated Sep. 24, 2014 in related International Preliminary Examining Authority application PCT/US2013/059703, 8 pages.
International Search Report dated Mar. 4, 2014 regarding PCT/US2013/059703, 4 pages.
International Preliminary Report on Patentability dated Dec. 8, 2014 in related PCT/US2013059703, 21 pages.
Patent Examination Report No. 1 dated Jan. 27, 2016 in related Australian Patent Application No. 2013315269, 6 pages.
Amtel Corporation; "ZigBee Pro Stack and Software Development Kit;" http://wwww.meshnetics/com/wsn-software/; 1 sheet.
Batcheldor; "Hospital Tries ZigBee to Track Patients;" RFID Journal; Jul. 21, 2006; pp. 1-2.
BelAir Networks; "Capacity of Wireless Mesh Networks;" White Paper; 2006; pp. 1-16.
Bogia; "Enabling The Future of u-Health-IEEE 11073 Personal Health Devide Standards;" Slides; Sep. 16, 2009; 38 slides.
Bowman; "Newly Ratified ZigBee Health Care Profile New Available for Public Download;" http://fiercehealthcare.com/node/40708/print; pp. 1-2.
Craig; "ZigBee Networks;" Medical Design; http://medicaldesign/com/electrical-components/zigbee_networks; Apr. 1, 2005; pp. 1-8.
Craig; "ZigBee: Wireless Control that Simply Works;" http://docs.zigbee.org/zigbee-docs/dcn/04-1427.pdf; prior to Jan. 2011; pp. 1-7.
Digi International Inc.; "ConnectPort® X4 H;" retrieved from the Internet: www.digi.com; 2008-2010; 2 sheets.
Digi International Inc.; "Demystifying 802.15.4 and ZigBee®;" White Paper; retrieved from the Internet: http://digi.com; 2008-2010; 5 sheets.
Digi International Inc.; "Xbee® & Xbee-PRO® ZB ZigBee® PRO RF modules;" http://digi.con/products/wireless/zigbee-mesh/xbee-zb-module.jsp; 1 sheet.
Digi International Inc.; "Xbee® & Xbee-Pro® ZB;" retrieved from the Internet: http://www/digi.com; 2008-2010; 2 sheets.
Dvorak; "Remote Monitoring;" http://medicaldesign.com/electrical/components/remote_monitoring/index.html; Apr. 1, 2005; pp. 1-4.
ENP Newswire; "Freescale Products Achieve ZigBee Health Care Certification;" www://allbusiness.com/health-care/health/care-facilities-nursing/14485133-1.html; May 19, 2010; 3 pages.
Huang; Medical Electronics: From Hospital and Clinic to the Home; http://www.eetimes.com/General/DisplayPrintViewContent?contentitemID=4211247; Dec. 5, 2010; pp. 1-6.
ICPDAS; ZigBee Converter User's Manual, Ver 1.0; Sep. 22, 2008; pp. 1-32.
Kawai et al.; "Proposal of an Assured Corridor Mechanism for Urgent Information Transmission in Wireless Sensor Networks;" IEICE Transactions on Communications, Communications Society, Tokyo, Japan; vol. E90B, No. 10; Oct. 1, 2007; pp. 2817-2826.
Le; "Designing Zig-Bee-Ready IEEE 802 15.4-Compiiant Radio Transceiver;" www.rfdesign.com; Nov. 2004; pp. 42-50.
Miche et al.; "The Internet of Vehicles of the Second Generation of Telematic Services;" ERCIM News, ERCIM, Paris, FR; vol. 77; Apr. 2, 2009; pp. 43-45.

(56) References Cited

OTHER PUBLICATIONS

Norris et al.; Single-Chip ZigBee for Indoor Mobile Telemetry; Presentation; Jun. 21, 2005; pp. 1-29
Pinto; "WMM—Wireless Mesh Monitoring," Technical Report; 2009; pp. 1-25.
Sailhan et al., :Wireless Mesh Network Monitoring: Design, Implementation and Experiments; In Proceedings of IEEE workshop on Distributed Autonomous Network Management (DANMS); 2007; pp. 1-6.
Skibniewski et al.; "Utiquitous Computing: Object Tracking and Monitoring in Construction Processing Utilizing Zigbee™ Networks;" $23^{rd}$ International Symposium on Automation and Robotics in Construction (ISCAR2006); Oct. 3-5, 2006; pp. 1-6.
Stewart; "ZigBee Build Reliable Zigbee-Based Solutions;" EE Times-Asia; Apr. 16-30, 2006; pp. 1-2.
Texas Instruments; Choose your ZigBee Solution with TI; 1Q 2010; 1 sheet.
Texas Instruments; Consumer Medical Applications Guide; retrieved from the Internet: http://www.ti.com/medical.; 2010 34 pages.
Texas Instruments; "RF/IF and ZigBee® Solutions;" http://focus/ti/com/analog/docs/gencontent/tsp?familyID=367
&genContent=ID24190&DC . . . ; Dec. 8, 2010; 2 sheets.
Texas instruments; ZigBee® Wireless Networking Overview; 1Q 2010; 1 sheet.
The Silicon Horizon, Inc.; TechFX ZigBee Tools v1.0; 2007-2008; pp. 1-52.
Tutorial-Reports.com; "Zigbee Tutorial;" http://www.tutorial-reports.com/book/print/152; Nov. 1, 2010; pp. 1-9.
Unknown Author; "The Nokia Network Monitor;" http://www.panuworkd.net/nuukieworld/misc/netmon/index/htm; Oct. 30, 2005; pp. 1-2.
Versel; "ZigBee Alliance Ratifies Wireless Protocol for Low-Power Medical Devices;" retrieved from the Internet: http://www.fiercemobilehealthcare.com/story/zigbee-alliance-ratifies-wireless-protocol-lo . . . ; Apr. 6, 2010; pp. 1-2.
Wellspring; Router, Tageway, Base Station, Cell Modem Specification and Submittal; http://h2odeegree.com/documents/ReferenceLibrary/OtherProductsLiterature/
RouterGatewayBaseSpecSheetsSubmittal.pdf; prior to Jan. 2011; 5 pages.
Wellspring; "Wellspring Switches to a ZigBee-Cellular Hybrid System;" Press Release; Feb. 20, 2006; pp. 1-3.
ZigBee® Wireless Sensor Application for Health, Wellness and Fitness; http://dics.zigbee.org/zigbee-docs/dcn/09-4962.pdf; Mar. 2009; pp. 1-15.
Office Action dated Sep. 5, 2013, for U.S. Appl. No. 13/006,769, 36 pages.
Office Action dated Dec. 27, 2013; for U.S. Appl. No. 13/352,575; 31 pages.
Office Action dated Jan. 7, 2014; for U.S. Appl. No. 13/353,565; 33 pages.
Office Action dated Nov. 16, 2012; for U.S. Appl. No. 13/037,8861 19 pages.
Response filed Feb. 14, 2013; for Office Action dated Nov. 16, 2012; for U.S. Appl. No. 13/037,8861 14 pages.
Final Office Action dated May 22, 2013; for U.S. Appl. No. 13/037,8861 15 pages.
Response filed Jul. 12, 2013; for Final Office Action dated May 22, 2014; 14 pages.
Notice of Allowance dated Oct. 9, 2013; for U.S. Appl. No. 13/037,886; 11 pages.
Request for Continued Examination filed Jan. 24, 2014; for U.S. Appl. No. 13/037,886; 2 pages.
Office Action; dated May 15, 2013; for U.S. Appl. No. 13/006,784; 35 pages.
Response filed Aug. 14, 2013; to Office Action dated May 15, 2013; for U.S. Appl. No. 13/006,784; 13 pages.
Final Office Action dated Dec. 2, 2013; for U.S. Appl. No. 13/006,784; 38 pages.
European Comments on Written Opinion dated Nov. 8, 2013; for EP Pat. App. No. 12708203.0; 2 pages.
PCT Search Report and Written Opinion of the ISA; for PCT Pat. App. No. PCT/US2012/021007; dated Sep. 20, 2012; 16 pages.
PCT International Preliminary Report on Patentability; dated Jul. 25, 2013; for PCT Pat. App. No. PCT/US2012/021007; 12 pages.
Article 19 Amendment; dated Nov. 16. 2012; for PCT Pat App. No. PCT/US2012/021007; 7 pages.
PCT Search Report and Written Opinion of the ISA for PCT Pat. App. No. PCT/US2012/068895; dated Mar. 15, 2013; 14 pages.
PCT Search Report and Written Opinion of the ISA; dated Apr. 1, 2013; for PCT Pat. App. No. PCT/US2012/068892; 12 pages.
PCT Search Report and Written Opinion of the ISA; for PCT Pat. App. No. PCT/US2013/020069; dated Feb. 1, 2013; 16 pages.
PCT Search Report and Written Opinion of the ISA; for PCT Pat. App. No. PCT/US2013/020071; dated Feb. 1, 2013; 10 pages.
PCT Search Report and Written Opinion of the ISA; dated Apr. 1, 2013; for PCT Pat. App. No. PCT/US2012/068888; 15 pages.
PCT Search Report and Written Opinion of the ISA; dated Dec. 3, 2012; for PCT Pat. App. No. PCT/2012/025906; 19 pages.
PCT International Preliminary Report on Patentability of the ISA; dated Sep. 12, 2013; for PCT Pat. App. No. PCT/US2012/025906; 14 pages.
Article 19 Amendment; dated Feb. 4, 2013; for PCT Pat. App. No. PCT/US2012/025906; 9 pages.
PCT Search Report and Written Opinion of the ISA; dated Apr. 29, 2013; for PCT Pat. App. No. PCT/US2013/021530; 10 pages.
PCT International Preliminary Report on Patentability; dated Jul. 25, 2013; for PCT Pat. App. No. PCT/US2012/021008; 7 pages.
PCT International Search Report; dated Aug. 2, 2012; for PCT Pat. App. No. PCT/US2012/021008.
Office Action dated Jul. 27, 2016 in related Chinese Application No. 201380047855.3, 21 pages.
Patent Examination Report No. 2 dated Aug. 1, 2016 in related Australian Application No. 2013315269, 5 pages.
Examiner's Report dated Aug. 8, 2016 in related Canadian Application No. 2,884,437, 4 pages.
Office Action dated Jan. 12, 2017 in related Korean Application No. 10-2015-7009012, 15 pages.
Patent Examination Report No. 3 dated Jan. 18, 2017 in related Australian Application No. 2013315269, 4 pages.

* cited by examiner

DOCKING STATION FOR AN ENTERAL FEEDING PUMP

CROSS-REFERENCE TO RELATED APPLICATIONS

This application is a national stage application of and claims the benefit of priority to International Patent Application No. PCT/US2013/059703, titled DOCKING STATION FOR ENTERAL FEEDING PUMP, filed on Sep. 13, 2013, which claims the benefit of priority to U.S. Patent Application No. 61/700,682, titled DOCKING STATION FOR AN ENTERAL FEEDING PUMP, filed on Sep. 13, 2012, each of which is incorporated herein by reference in its entirety for all purposes.

BACKGROUND

Field

The present disclosure is directed to a remote monitoring system for monitoring medical devices in communication with a wireless communication network, and more particularly, to a remote monitoring system having a plurality of monitoring devices for monitoring medical devices that communicate with the wireless communication network via one or more wireless relay modules and a wireless relay network.

Related Art

In critical care and home care health service centers, including hospitals, clinics, assisted living centers and the like, care giver-patient interaction time is at a premium. Moreover, response times by care givers to significant health conditions and events can be critical. Systems of centralized monitoring have been developed to better manage care giver time and patient interaction. In such systems, physiological data from each patient is transmitted to a centralized location. At this centralized location, a single or small number of technicians monitor all of this patient information to determine patient status. Information indicating a patient alarm condition will cause the technicians and/or system to communicate with local care givers to provide immediate patient attention, for example via wireless pagers and/or cell phones, and/or by making a facility-wide audio page.

Implementing such centralized monitoring systems using wireless networks may present a number of difficulties. In order to effectively monitor patient status using information provided by a variety of medical devices that may be dynamically assigned to patients in a variety of rooms and on a variety of floors in a facility, it would be desirable to establish communications between the medical devices and the centralized location by means of a local area network such as, for example, a "WiFi" network based on IEEE 802.11 standards. However, as such networks are typically already in place in facilities to support a variety of other functions (for example, physician access to electronic medical records (EMRs), facility administrative systems and other functions), it is often undesirable to secure sufficient local area network access for the purpose of providing centralized monitoring. Moreover, when a patient is located remotely from a critical care health service center (for example, at home), access to traditional local area network facilities such as a WiFi network may be unavailable or not sufficiently reliable to support critical care monitoring applications.

For improved efficiencies in centralized monitoring of critical care and home care health service centers, it may be desirable to provide a single "off-site" centralized monitoring location for monitoring several geographically-dispersed critical care health service centers.

As an alternative to conventional WiFi or IEEE 801.11-based local area networks, ZIGBEE networks based on the IEEE 802.15.4 standard for wireless personal area networks have been used for collecting information from a variety of medical devices in accordance with IEEE 11073 Device Specializations for point-of-care medical device communication, including for example pulse oximeters, blood pressure monitors, pulse monitors, weight scales and glucose meters. See, e.g., *ZIGBEE Wireless Sensor Applications for Health, Wellness and Fitness*, the ZIGBEE Alliance, March 2009, which is incorporated by reference herein in its entirety. As compared to present IEEE 802.15.1 Bluetooth wireless personal area networks, for example, ZIGBEE networks provide the advantage of being dynamically configurable, for example, in "self-healing" mesh configurations, and operating with low power requirements (enabling, for example, ZIGBEE transceivers to be integrally coupled to the medical devices under battery power). However, transmission ranges between individual ZIGBEE transceivers are generally limited to no more than several hundred feet. As a consequence, such networks are suitable for on-site communications with medical devices, but unusable for centralized monitoring locations located off-site.

Therefore, a hybrid system may be employed in which one or more wireless personal area networks are configured to facilitate on-site communications between medical devices and one or more wireless relay modules which are further configured to communicate with off-site centralized monitoring systems (for example, via a wireless wide-area network (WWAN) such as a mobile telephone data network, for example, based on a Global System for Mobile Communications (GSM) or Code Division Multiple Access (CDMA) cellular network or associated wireless data channels). Such a relay module and system are respectively described in the related patent applications entitled "Wireless Relay Module for Remote Monitoring Systems," U.S. patent application Ser. No. 13/006,769, filed Jan. 14, 2011 and "Medical Device Wireless Network Architectures," U.S. patent application Ser. No. 13/006,784, filed Jan. 14, 2011, each of which is incorporated herein by reference for all purposes.

In accordance with applicable patient data privacy provisions of the Health Insurance Portability and Accountability Act of 1996 (HIPAA), communication of information between the monitored medical devices and the central monitoring location must be done securely, and medical device and associated patient information must be made available only to personnel accessing the centralized monitoring systems who are in possession of the appropriate access credentials. In order to be viable, the centralized monitoring system must also be capable of recognizing medical device information indicating an alert condition requiring response by on-site or other specialized personnel and reaching those on-site or specialized personnel to report the alert condition in a timely fashion.

Thus, it would be desirable to provide a remote, centralized medical information monitoring system that communicates over a wireless network of wide reach (for example, a wireless wide area network) with one or more critical care and/or home care health service centers via one or more wireless relay modules at each site, where the wireless relay modules relay communications provided by on-site medical devices over a wireless local area network or wireless personal area network. It would further be desirable for the centralized medical information monitoring system to be capable of also configuring medical devices according to associations with individual sites and patients, of logging communications from medical devices, of displaying medical device data to users of the centralized medical information monitoring system who are able to provide sufficient credentials, and of recognizing medical device alert conditions and reporting these conditions to responsible personnel in a timely fashion.

SUMMARY

Described herein are concepts, systems, circuits and techniques for a docking station configured to couple to an enteral feeding pump or other medical device. In one embodiment, the docking station includes a wireless transmitter for communicating data, such as operating parameters and/or status, to a remote monitor over a wireless communication link, to permit remote monitoring of certain pump diagnostics. In some embodiments, the docking station may utilize the wireless communication link to permit control and/or data exchange with the feeding pump. This may be in addition to or in place of the remote monitoring. The pump may also contain a receiver for receiving data such as operating parameter instructions, general operating instructions, and/or commands.

In one embodiment the wireless communication link may be provided utilizing cellular telephony technology. In other embodiments other wireless communication technologies may be used including, but not limited to any wireless technology based, in whole or in part, upon the IEEE 802.11 standards. For example, WiFi technology, Blue Tooth technology, ZigBee technology may be used.

In accordance with the concepts, systems, circuits and techniques described herein, a docking station for an enteral feeding pump includes a base portion and side portions projecting from the base portion. The base and side portions have surfaces configured to accept the enteral feeding pump. The docking station further includes a latch configured to secure the enteral feeding pump to the base portion and a release mechanism configured to release the enteral feeding pump from the base portion. The docking station further includes a communication/power port disposed on one of the base or side surfaces and configured to couple to a mating port provided on the enteral feeding pump. The docking station further includes a wireless communication module configured to perform wireless communications and a charging module which provides power to the enteral feeding pump, e.g. to charge a power source within the enteral feeding pump.

With this particular arrangement, a docking station having with wireless communication and configured to couple to an enteral feeding pump is provided. In one embodiment the wireless communication module of the docking station enables wireless communication with one or all of: a local hospital network; an intranet; an internet; and/or a remote device or system. Thus, when the docking station receives data and other information from the pump, the docking station communicates the data and information to nurses, health care providers and healthcare equipment companies via one or more network communication links. Also, the docking station may communicate with the pump via a wired connection or via a wireless connection. Thus the docking station allows the enteral feeding pump to communicate wirelessly with the docking station and in turn with other remote devices and/or destinations in a network.

Furthermore, while also communicating with the pump, the docking station also charges the pump via a docking station charging module.

In one embodiment, the base portion of the docking station includes the wireless charging module.

In one embodiment, the docking station is provided having a size, shape and configuration which allowed the docking station to be disposed on a flat surface such as a tabletop.

In one embodiment, the base portion includes a support device (e.g. a clamp) which allows the docking station to be clamped to another object such as an IV pole or some other mobile support unit (e.g. a wheelchair).

In one embodiment, the docking station further comprises a WIFI/cellular wireless board inside the base portion. By disposing the WIFI/cellular wireless board inside the base portion, (as opposed to having the WIFI/cellular wireless board internal to the enteral pump), the enteral feeding pump remains relatively small and light (and thus ambulatory) while still providing wireless communication capability. Thus, a wireless docking station and enteral feeding pump combination is provided in which the size and weight of the enteral feeding pump is such that the enteral feeding pump remains ambulatory while still providing wireless communication capability.

In one embodiment, the wireless module is integral to the base portion. This provides user benefit because by making the wireless module integral to the base portion it will be readily noticeable and difficult to lose the wireless module. Furthermore, in some embodiments, the wireless module provides communication capability and also charges the enteral feeding pump.

In some embodiments, the docking station further comprises means for quick disconnection from the IV pole for ambulatory use. In ambulatory cases, it may be beneficial to have the pump provide power to the wireless module via the direct power connection when AC power is not available. This feature provides freedom and mobility to the wireless module allowing wireless access with the patient is going about daily activities where direct AC power is not available.

In one embodiment, the docking station described herein includes a charging base having the necessary electrical circuitry and mechanical structures to perform a charging function as well as: (1) providing a direct physical linkage or docking of the pump with the wireless module charging base; (2) during this direct linkage, the charging base provides power to the pump to ensure that rechargeable power sources (e.g. rechargeable batteries) on the pump receive charging while attached to the charging base; (3) the charging base will have a quick disconnect pole clamp that allows the charging base to be attached to the IV pole and then easily removed via quick disconnect so the wireless module can be used ambulatory with the pump. This would leave a portion of the pole clamp still affixed to the IV pole. This also allows for easy reconnection to the IV pole after ambulatory use; (4) the charging base can have the alternate ability to receive power for wireless communication via the direct link to the pump in an ambulatory situation. In this condition, the backup battery on the pump could provide sufficient power to send wireless signals when no AC power is available; (5) it is further possible that the charging base would contain its own rechargeable battery in the event that the charging base moves with the pump in an ambulatory/backpack situation; (6) In similar fashion to 4, the pump could receive extra battery life using the battery in the charging base; (7) the base module will have the capability to sit on a tabletop or be clamped to an IV pole.

A docking station as described herein allows the size and weight of an enteral feeding pump to remain small (and thus ambulatory) while still providing wireless communication capability. This is due to the storage of one or more WIFI/cellular wireless boards inside the charging base as opposed to having the WIFI/cellular wireless board internal to the pump.

The base module provides a user benefit, that it will be difficult to lose the wireless module since it will be integral to the charging base and typically would be located on user accessed equipment or appliance such as any of a table, bedframe, a wheelchair, and an IV pole. The base module typically charges the battery in the pump.

The base module can include means for mounting to an IV pole. In some cases, the base module allows for quick disconnection from the IV pole for ambulatory use. In ambulatory cases, it may be beneficial to have the pump provide power to the wireless module via the direct power connection when AC power is not available. This is a great advantage in that it provides freedom and mobility to the wireless module allowing wireless access with the patient is going about daily activities where direct AC power is impractical. Including a battery with the charging base also provides the benefit of providing wireless communication directly from the base in ambulatory situations, but also, could possibly provide additional battery life to the pump while it maintains its direct power linkage to the pump.

In one embodiment, the feeding pump may also contain a wireless transmitter for communicating data, such as operating parameters and/or status, to a remote monitor over a wireless communication link, preferably utilizing cellular telephony technology to permit remote monitoring of certain pump diagnostics. The feeding pump may also contain a receiver for receiving data such as operating parameter instructions, general operating instructions, and/or commands.

BRIEF DESCRIPTION OF THE DRAWINGS

The foregoing features of the invention, as well as the invention itself may be more fully understood from the following detailed description of the drawings, in which.

DETAILED DESCRIPTION

Reference will now be made in detail to exemplary embodiments of the invention, including the best modes contemplated by the inventors for carrying out the invention. Examples of these exemplary embodiments are illustrated in the accompanying drawings. While the invention is described in conjunction with these embodiments, it will be understood that it is not intended to limit the invention to the described embodiments. Rather, the invention is also intended to cover alternatives, modifications, and equivalents as may be included within the spirit and scope of the invention as defined by the appended claims.

In the following description, specific details are set forth in order to provide a thorough understanding of the present invention. The present invention may be practiced without some or all of these specific details. In other instances, well-known aspects have not been described in detail in order not to unnecessarily obscure the present invention.

For the purpose of illustrating the present invention, exemplary embodiments are described with reference to FIGS. 1-5.

In this specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

Figure 1:
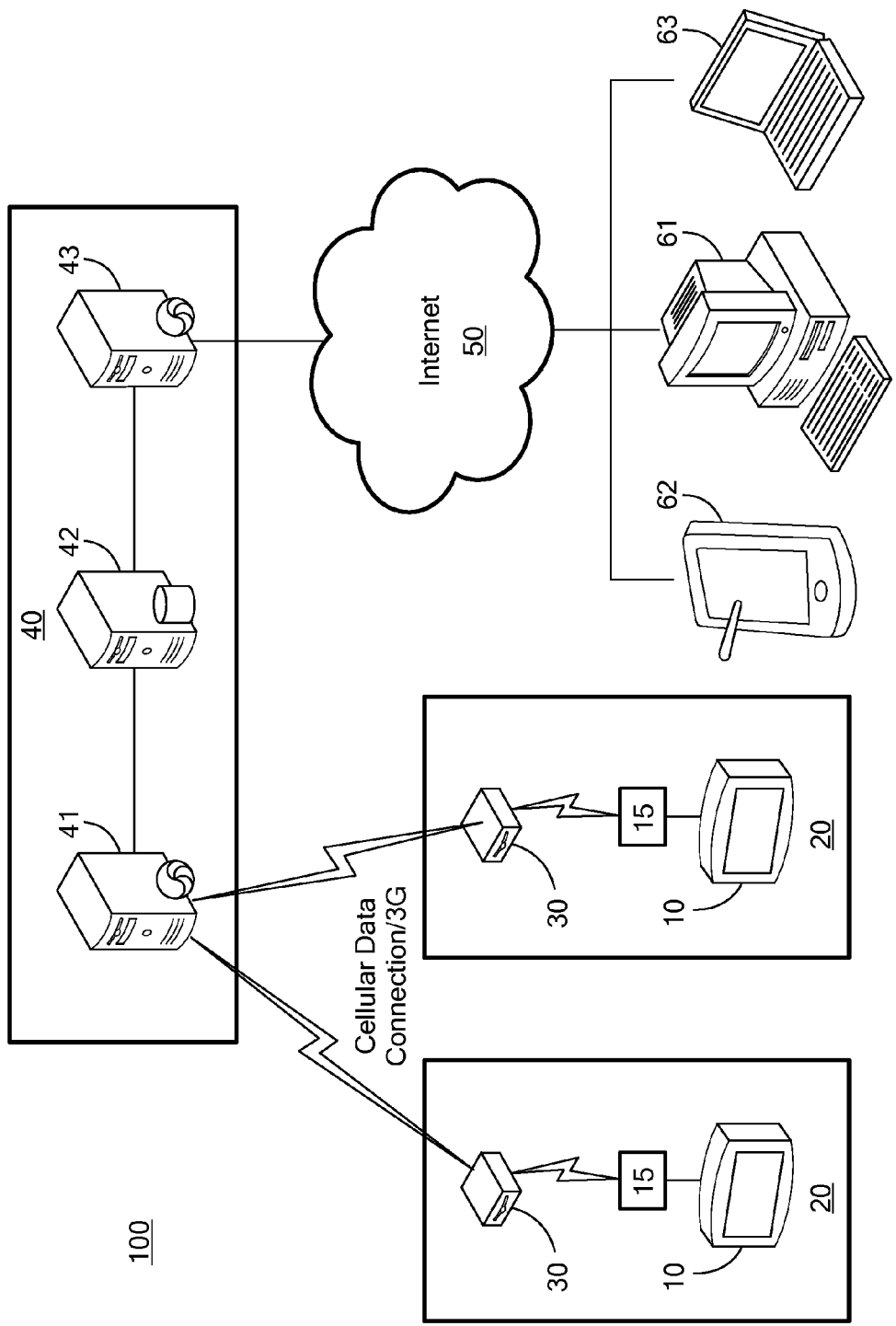
FIG. 1 present a schematic diagram of an exemplary architecture for a system for monitoring a medical device according to the present invention.

A schematic diagram of an exemplary architecture 100 for a system for monitoring medical devices in accordance with the present invention is illustrated in FIG. 1. One or more medical devices 10 are provided at a patient facility 20 for monitoring the medical condition and/or administering medical treatment to one or more patients. Patient facility 20 may comprise a critical care health service center (for example, including hospitals, clinics, assisted living centers and the like) servicing a number of patients, a home facility for servicing one or more patients, or a personal enclosure (for example, a backpack) that may attached to or worn by an ambulatory patient. Associated with each medical device 10 is an interface circuit interface circuit 15 that includes a transceiver for transmitting and receiving signals in a facility-oriented wireless network such as, for example, a Low-Rate Wireless Personal Area Networks or "LR-WPAN," ZIGBEE network or other low-power personal area networks such as the low power Bluetooth networks, e.g., Bluetooth 2.0, existing or presently under development or consideration. It should be understood that interface circuit 15 may be contained within or disposed external to medical device 10 in accordance with the present invention. Also provided within the patient facility 20 are one or more relay modules 30

Figure 2:
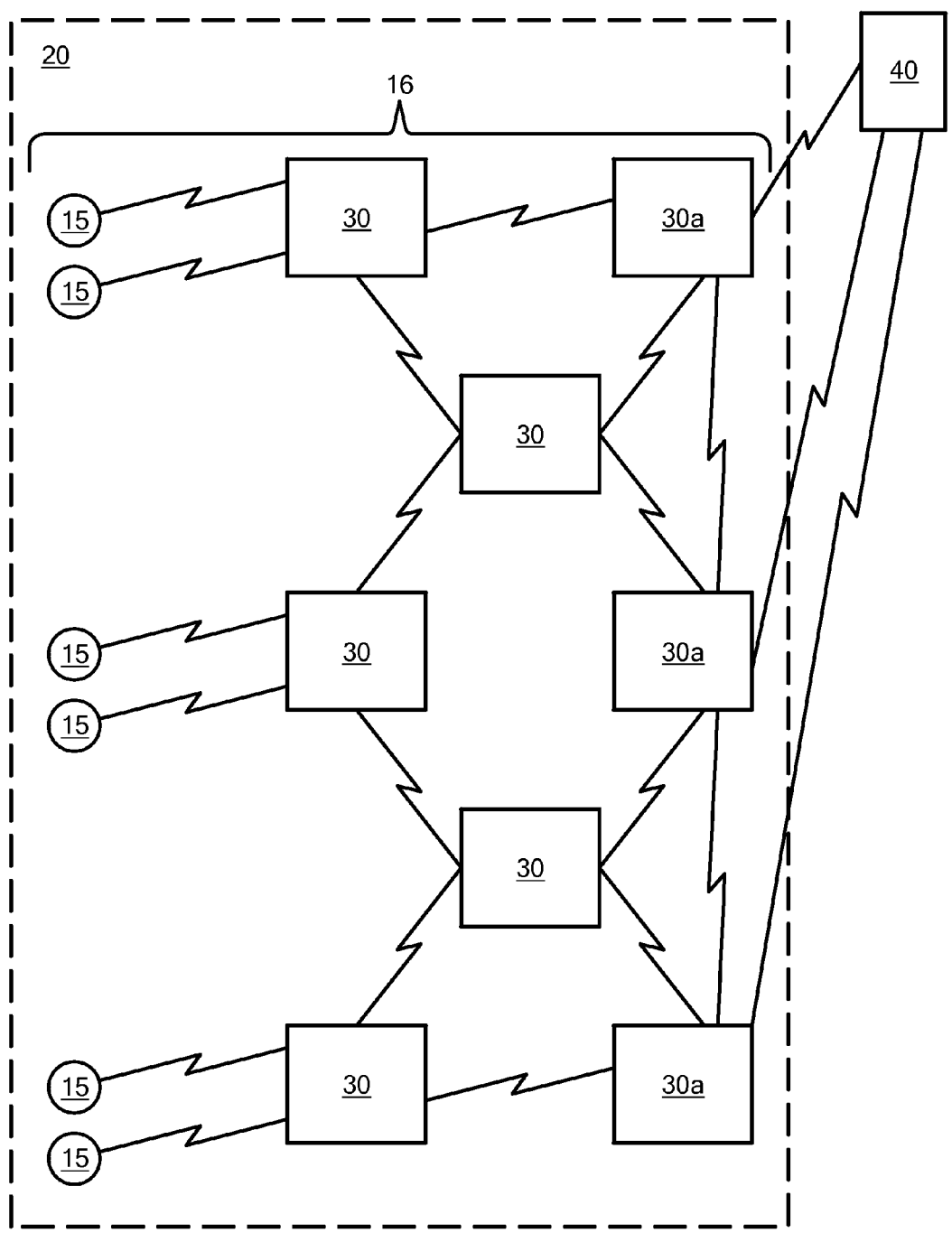
FIG. 2 presents a schematic diagram further illustrating exemplary wireless network components of the architecture according to FIG. 1.
Figure 3:
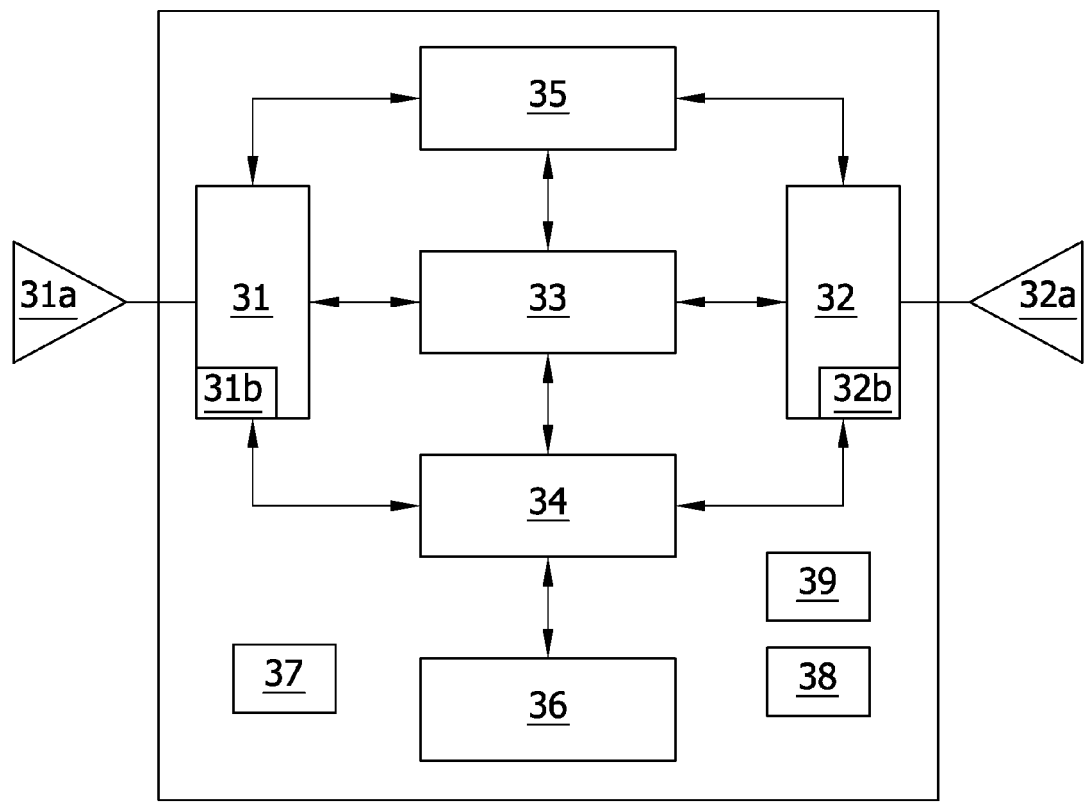
FIG. 3 presents a schematic diagram illustrating an exemplary wireless relay module associated with the architecture according to FIG. 1.

As described in greater detail with regard to FIG. 3, each module 30 includes a first transceiver for receiving signals from and transmitting signals to the interface circuits 15 in the facility-oriented wireless network. Relay modules 30a as depicted in FIG. 3 correspond to relay modules 30, and further include a second transceiver for wirelessly transmitting signals to and receiving signals from an access point 40 as shown in FIG. 2 via a wireless wide-area network or "WWAN". Suitable WWANs for use with the present invention include, for example, networks based on a Global System for Mobile Communications (GSM) or Code Division Multiple Access (CDMA) cellular network or associated with the 2G, 3G, 3G Long Term Evolution, 4G, WiMAX cellular wireless standards of ther International Telecommunication Union-Radiocommunication Sector (ITU-R). For compliance with HIPAA regulations, communications over each of the facility-oriented wireless network and WWAN are preferably conducted securely using, for example, using a Secure Sockets Layer (SSL) protocol or a Transport Layer Security (TLS) protocol.

As illustrated in FIG. 1, a suitable access point 40 useable with the present invention may include an inbound web server 41 that incorporates or otherwise has access to a transceiver for communicating with the relay modules 30a over the WWAN. Medical device data received by the inbound web server 41 over the WWAN is forwarded to a secure data storage server 42, which is configured for example to log the received data in association with identification information of the associated medical devices. An outbound web server 43 is configured, for example, to receive and qualify data retrieval requests submitted by one or more of remote monitoring devices 61, 62 and 63 over a broad-band network 50 (for example, over the Internet), to request associated medical device data to be retrieved from the secure data storage server 42, and to format and transmit the retrieved data to the one or more remote monitoring devices 61, 62 and 63 for display on associated device displays. While this disclosed architecture for the access point 40 is illustrated with an exemplary embodiment of the present invention, it should be understood that any architecture for the access point 40 that enables the receipt, storage and retrieval of medical device data on a device display of the one or more remote monitoring devices 61, 62 and 63 is intended to be included within the scope of the present invention.

FIG. 2 presents a block diagram that further illustrates exemplary components of the inventive architecture that are located within or otherwise associated with the patient facility 20 of FIG. 1. In FIG. 2, a number of interface circuits 15 and relay modules 30, 30a are arranged in a mesh network 16 within the patient facility 20. The interface circuits 15 and relay modules 30, 30a are configured to communicate with one another via associated wireless links. In a preferred embodiment of the present invention represented in FIG. 2, the network 16 is a ZIGBEE mesh network based on IEEE 802.15.4. However, the network 16 may be organized according to a variety of other wireless local area network (WLAN) or WPAN formats including, for example, WiFi WLANs based on IEEE 802.11 and BLUETOOTH WPANs based on IEEE 802.15.1.

In the illustrated ZIGBEE mesh network 16, each of the interface circuits 15 includes a communications interface such as, for example, a wired communications interface, to an associated medical device 10. In addition, each of the relay modules 30, 30a includes at least one transceiver configured to communicate with other relay modules 30, 30a in the ZIGBEE mesh network 16. Relay modules 30a further include at least a second transceiver for communicating over the WWAN with the access point 40.

The ZIGBEE mesh network 16 provides the advantages of being self-configurable when one or more interface circuits 15 and/or relay modules 30, 30a are added to the network, and self-healing when one or more interface circuits 15 and/or relay modules 30, 30a are removed from or otherwise disabled in the network. Sub-groupings of the interface circuits 15 and relay modules 30, 30a may be provided in a defined geographic space (for example, on an individual floor or within a region of a floor in a multi-floor home or care facility).

FIG. 3 provides a block diagram illustrating exemplary components of relay module 30a. The relay module 30a of FIG. 3 includes a first transceiver 31 for wirelessly communicating with interface circuits 15 and other relay modules 30, 30a in the WLAN or WPAN network 16 of FIG. 2 via an antenna 31a. The relay module 30a further includes a second transceiver 32 for wirelessly communicating with the access point 40 over the WWAN via an antenna 32a. Each of the transceivers 31, 32 is in communication with a data processing circuit 33, which is configured to operate under the control of a processor 34 to accept data received by the transceivers 31, 32 and store the received data in a buffer element 35. In addition, the data processing circuit 33 is further configured to retrieve data from the buffer element 35 under the direction of the processor 34 and provide the retrieved data to a selected one of the transceiver 31 or transceiver 32 for transmission. In order to make a selection, the processor 34 is configured to communicate with respective status modules 31b, 32b of the transceivers 31, 32 in order to determine a communications status of each of the transceivers 31, 32.

The processor 34 is also preferably in communication with an input/output circuit 36, which provides signals to one or more display elements (not shown) of the relay module 30a, for example, for indicating a start-up or current status of the relay module 30a, including communication or connection status with the WLAN or WPAN network 16 and WWAN. The input/output circuit 36 may also be connected to user buttons, dials or input mechanisms and devices of module 30a. The input/output circuit 36 is further usable for providing alarm signals to indicate, for example, A/C power loss or loss of accessibility to the WWAN or wireless relay network.

Relay module 30a may preferably be provided as a small physical enclosure (not shown) with an integral power plug and power supply circuit 37, such that the relay module 30a may be directly plugged into and supported by a conventional wall outlet providing commercial A/C power. Relay module 30a may also preferably include a battery back-up circuit 38 to provide uninterrupted power in the event of A/C power outage as well as for ambulatory use of the relay module. Alternatively, relay module 30a may be provided with rechargeable and/or replaceable battery power 39 as a primary power source for ambulatory use.

Figure 4:
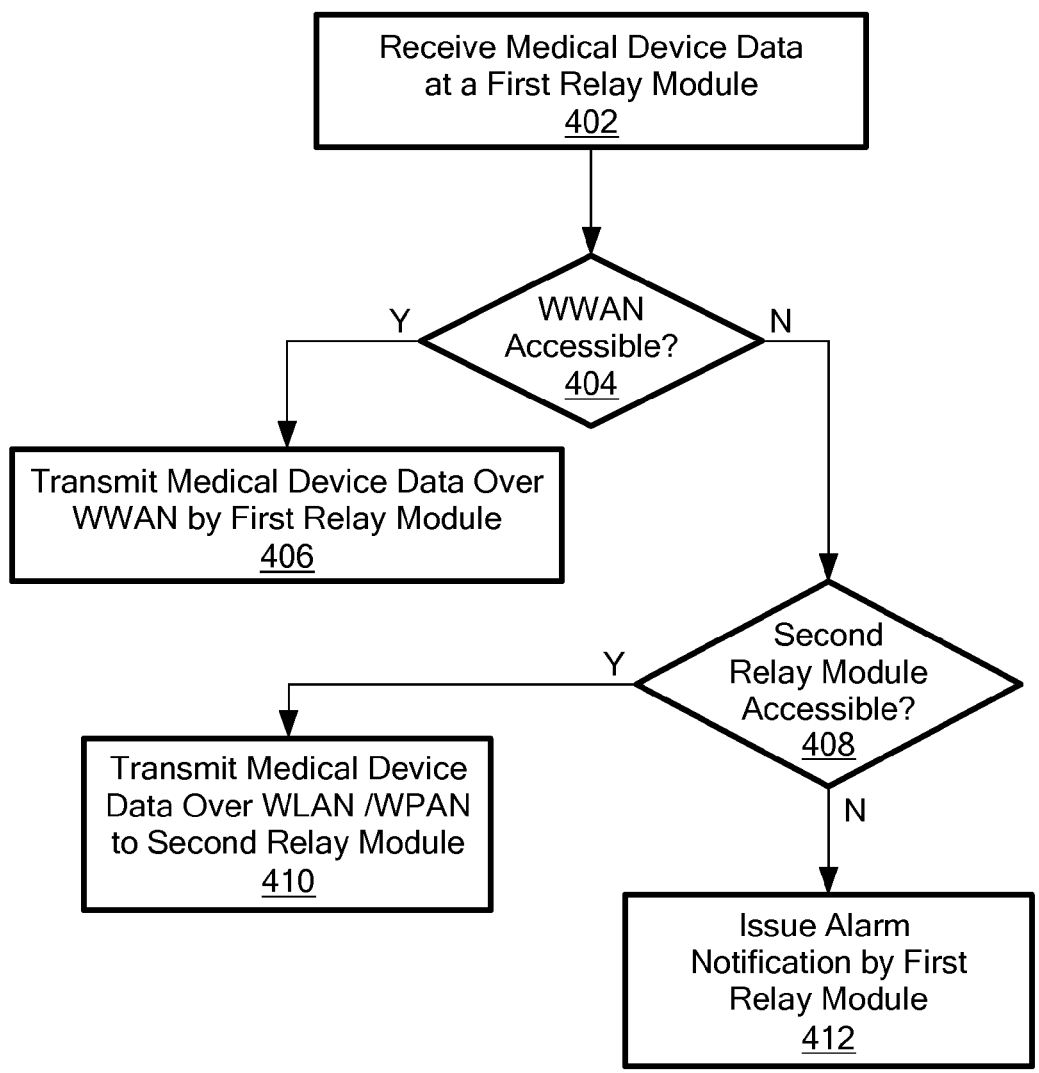
FIG. 4 presents a flow diagram illustrating a first exemplary method of operation for the architecture according to FIG. 1.

FIG. 4 presents a flow diagram illustrating an exemplary method of operation 400 for the architecture according to FIG. 1 and relay module 30, 30a components of FIGS. 2, 3, relating to the transmission of medical device data obtained from a medical device 10 to the access point 40. At step 402 of the method 400, the medical device data is received at a first one of the relay modules 30a from one of the interface circuits 15 and/or other relay modules 30, 30a over the ZIGBEE mesh network 16. At step 404, the processor 34 of the one relay module 30a determines whether the WWAN is accessible by that relay module 30a.

The determination of step 404 may be carried out in a variety of manners. For example, the processor 34 may interrogate the status module 32b of the transceiver 32 at the time of the receipt of the medical device data to determine a status of access for the transceiver 32 to the WWAN (for example, as the result of the transceiver 32 detecting an access signal of the WWAN having adequate signal strength). Alternatively, the processor 34 may interrogate the status module 32b at a different time including, for example, at system start-up and/or periodically (for example, hourly), and maintain a status indicator such as in the buffer 35 or another storage element to be retrieved at the time of receipt of the medical data. As yet another alternative, the relay module 30, 30a may be assigned a predetermined, fixed role within the network 16. For example, relay modules 30a in the network 16 may be assigned a data routing assignments by a controller or "master" relay module. By definition, the WWAN status for relay module 30 that does not possess WWAN access capability shall have a fixed status of "WWAN inaccessible."

If, as provided for in step 404, the status module 32b indicates that the WWAN is accessible by the transceiver 32, then the processor 34 will proceed to step 406 to instruct the data processing circuit 33 of the one relay module 30 to retrieve the medical device data from the buffer 35 (as necessary) and forward the medical device data to the transceiver 32 for transmission to the access point 40 over the WWAN.

Alternatively, in step 404, the status module 32b may indicate that the WWAN is not accessible by the transceiver 32. For example, if the one relay module 30a is located on a basement floor of the building in an area that is substantially shielded with respect to WWAN signals, the WWAN may not be accessible to the one relay module 30a. In this event, at step 408, the processor 34 determines whether a second relay module 30a is accessible via the WLAN or WPAN. Again, this determination may be made in a variety of manners including by instructing the transceiver 31 to send a handshake signal transmission directed to a second relay module 30a and to listen for a reply, or by retrieving a stored status indicator for the second relay module 30a.

If the second relay module 30a is accessible, then the processor 34 instructs the data processing circuit 33 of the one relay module 30a to retrieve the medical device data from the buffer 35 (as necessary) and forward the medical device data to the transceiver 31 for transmission to the second relay module 30a over the WLAN or WPAN at step 410. Alternatively, if the second relay module 30a is inaccessible in step 408, this portion of the process 400 may preferably be repeated to search for a further relay module 30a that is accessible. Alternatively, or in the event that no other relay module 30a is available, the processor 34 of the one relay module 30a may preferably issue an alarm notification at step 412. Such an alarm notification may, for example, include one or more of local visual and audio alarms as directed by processor 34 via the input/output circuit 36 of the one relay module 30a, alarm messages directed by the processor 34 to another accessible WPAN, WLAN or WWAN via one or more of the transceivers 31, 32, and/or alarm messages generated by the the inbound web server 41 of the access point 40 of FIG. 1 after a specified time period has been exceeded during which a handshake signal of the relay module 30a is due to be received at the inbound web server 41.

Figure 5:
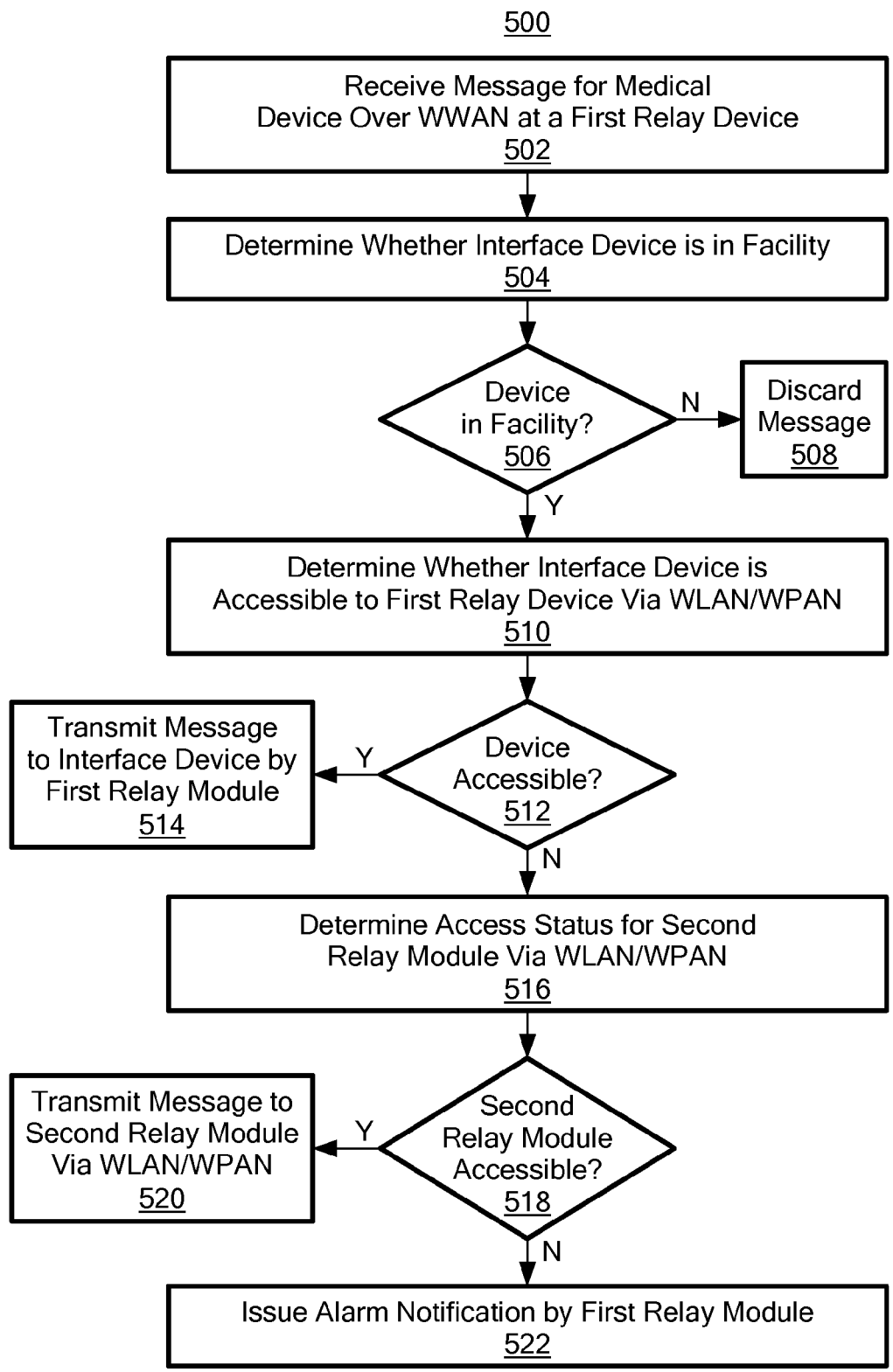
FIG. 5 presents a flow diagram illustrating a second exemplary method of operation for the architecture according to FIG. 1.
Figure 6:
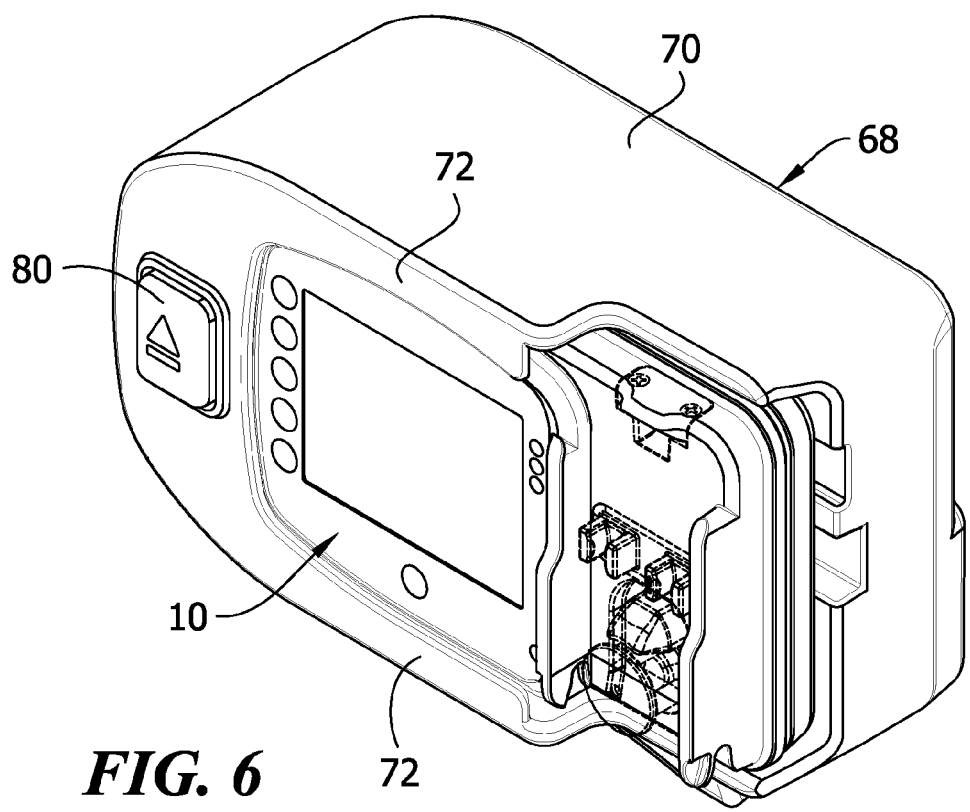
FIG. 6 is a schematic illustration showing a front perspective view of an enteral feeding pump in a docking station as a medical device that may be utilized in the architecture of FIG. 1.
Figure 7:
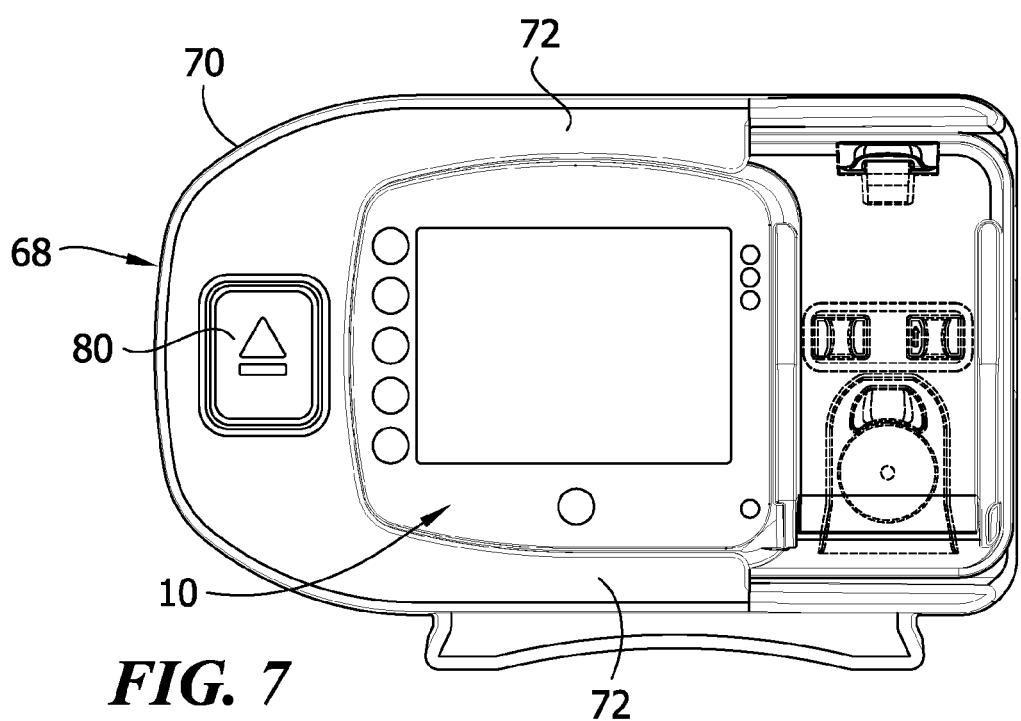
FIG. 7 is a schematic illustration showing a front elevational view of the pump in the docking station of FIG. 6.
Figure 8:
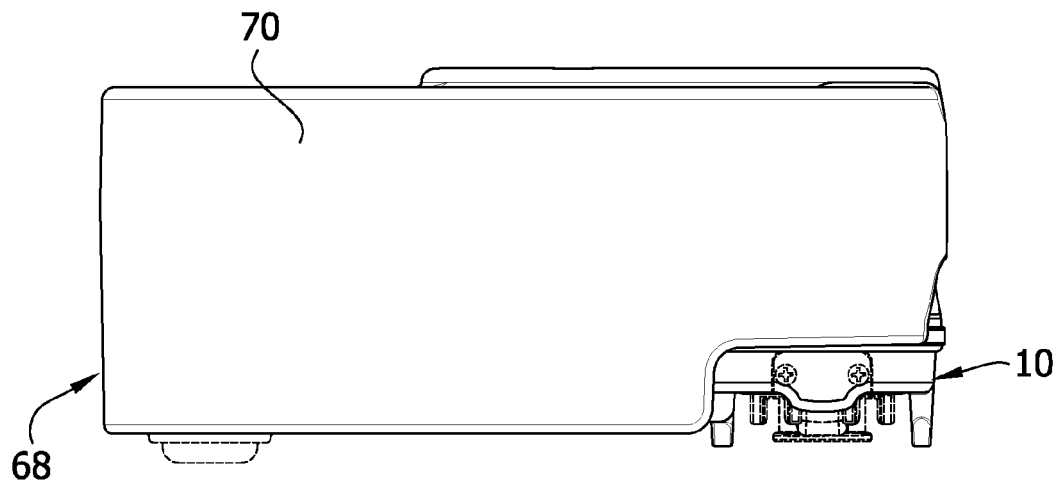
FIG. 8 is a schematic illustration showing a top plan view of the pump in the docking station of FIG. 6.
Figure 9:
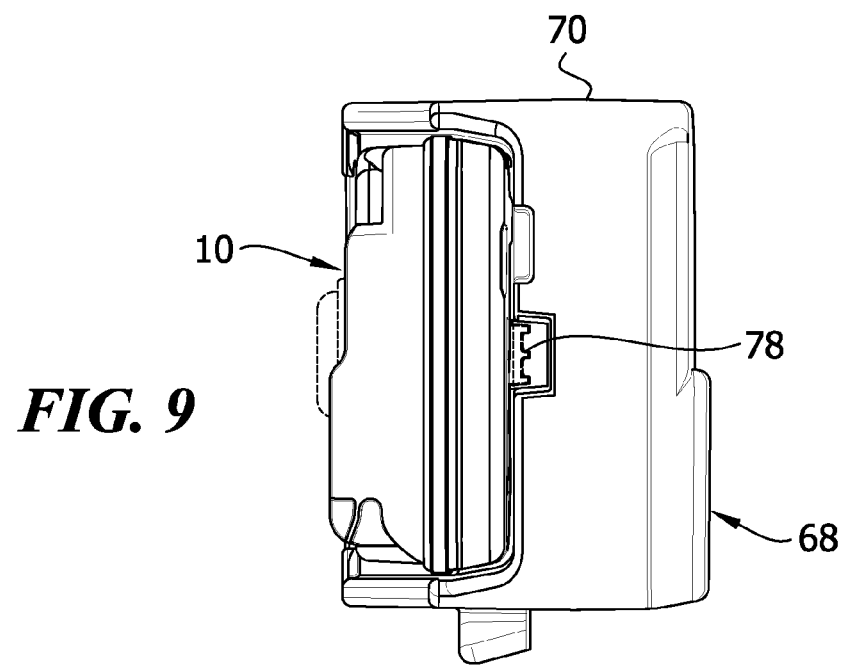
FIG. 9 is a schematic illustration showing a right side elevation view of the pump in the docking station of FIG. 6.
Figure 10:
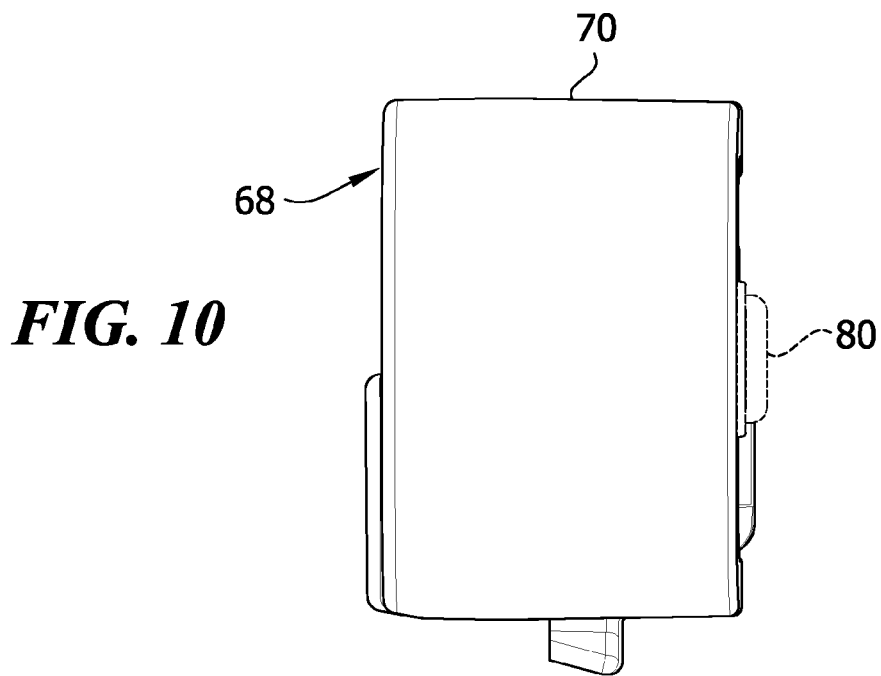
FIG. 10 is a schematic illustration showing a left side elevation view of the pump in the docking station of FIG. 6.
Figure 11:
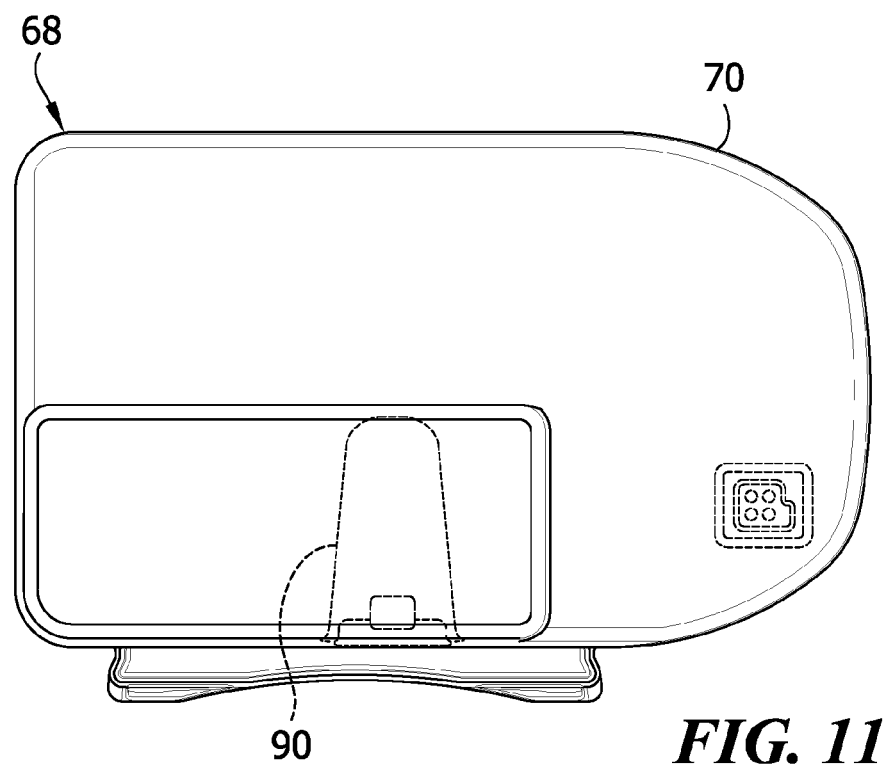
FIG. 11 is a schematic illustration showing rear elevation view of the docking station of FIG. 6.
Figure 12:
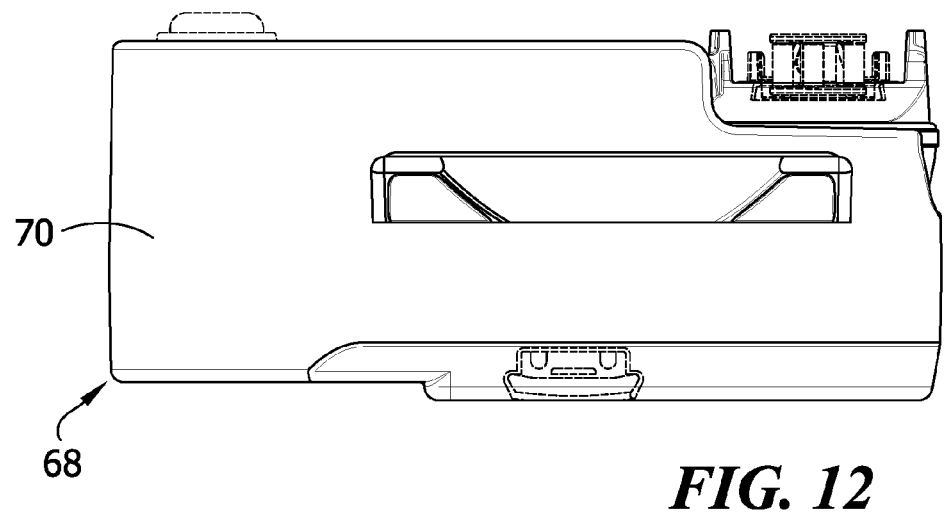
FIG. 12 is a schematic illustration showing bottom plan view of the pump in the docking station of FIG. 6.
Figure 13:
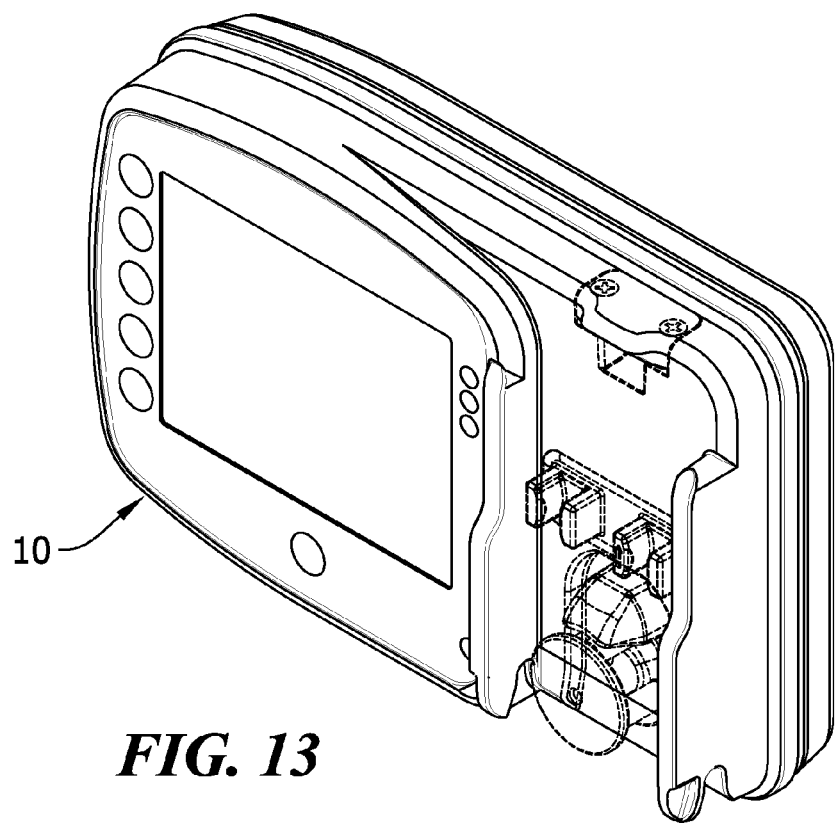
FIG. 13 is a schematic illustration showing a front perspective view of the pump (without the docking station) of FIG. 6.
Figure 14:
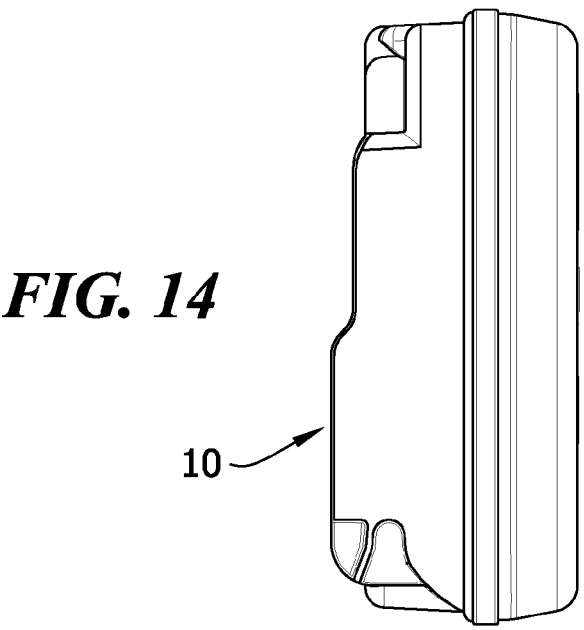
FIG. 14 is a schematic illustration showing a right side elevational view of the pump of FIG. 13.
Figure 15:
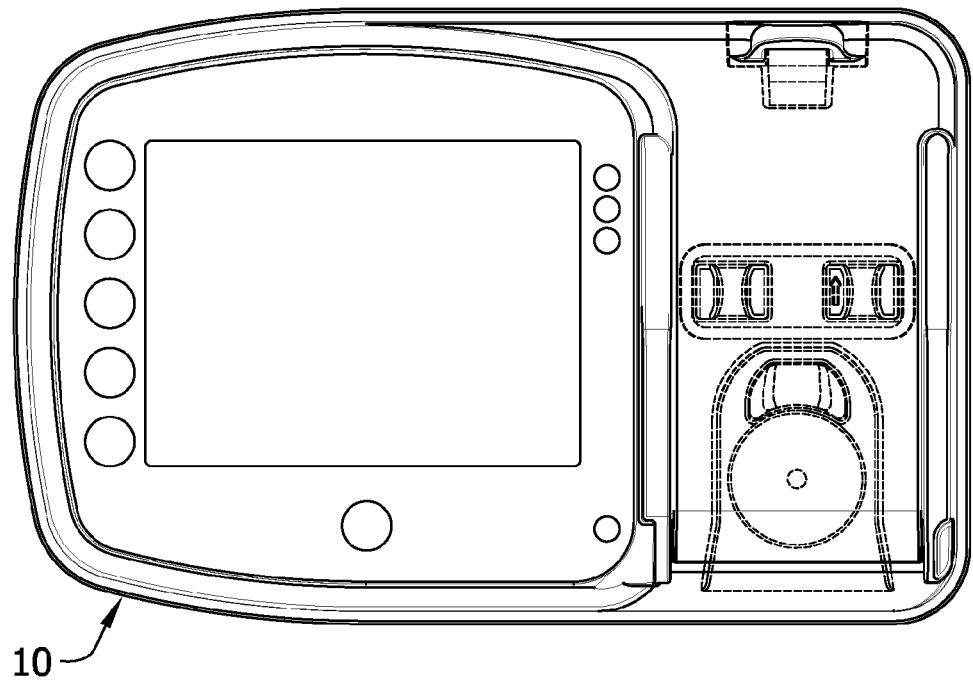
FIG. 15 is a schematic illustration showing a front elevational view of the pump of FIG. 13.
Figure 16:
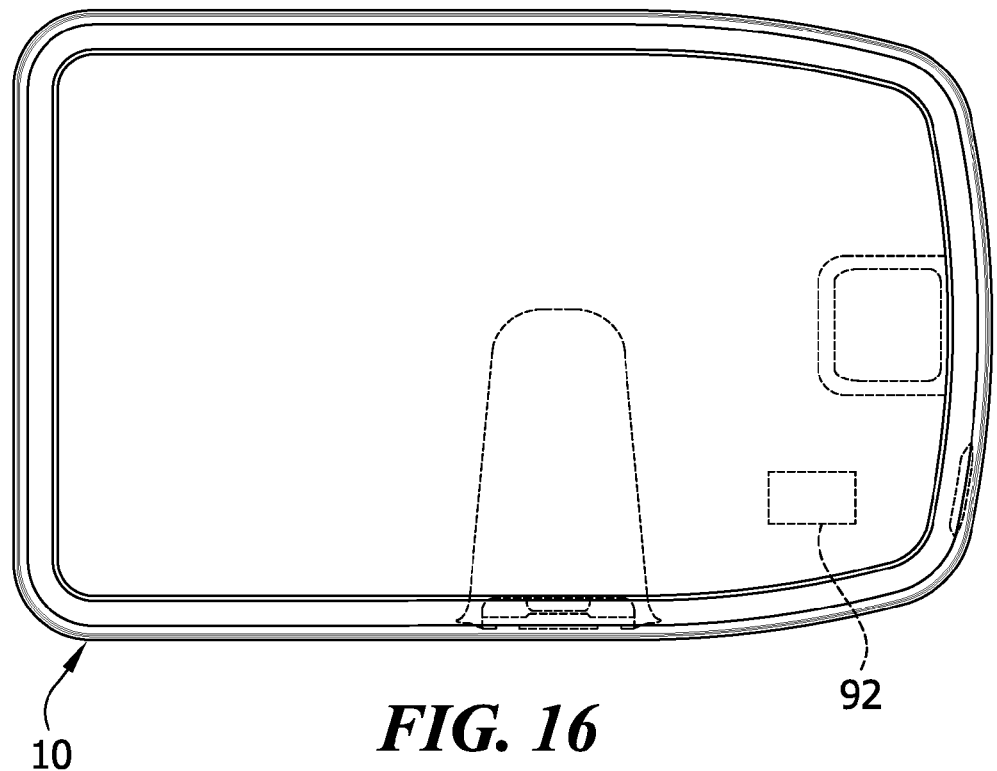
FIG. 16 is a schematic illustration showing a rear elevational view of the pump of FIG. 13.
Figure 17:
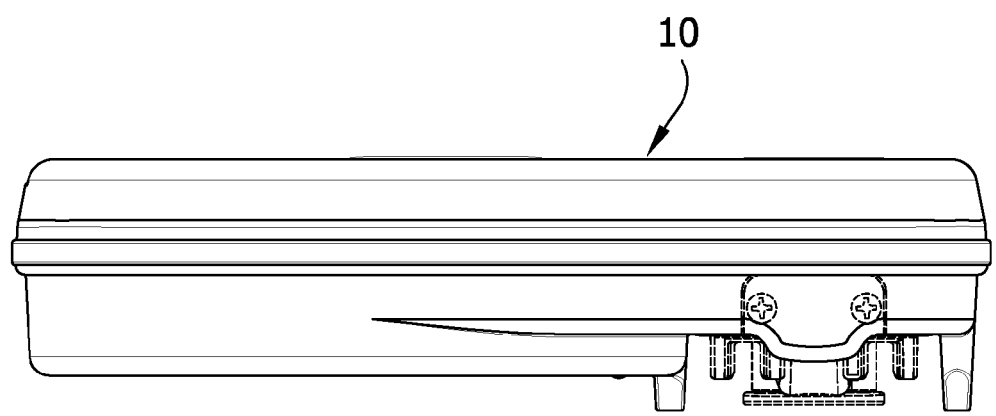
FIG. 17 is a schematic illustration showing a top plan view of the pump of FIG. 13.
Figure 18:
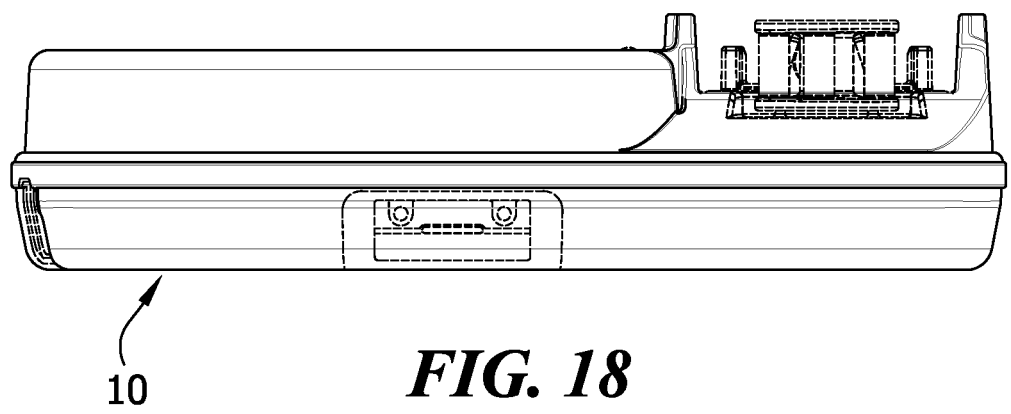
FIG. 18 is a schematic illustration showing bottom plan view of the pump of FIG. 13.
Figure 19:
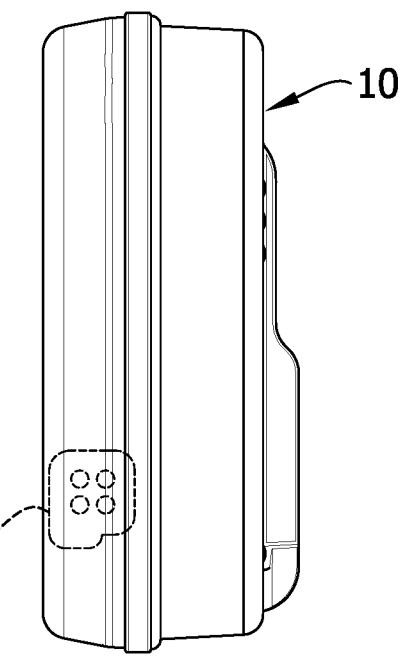
FIG. 19 is a schematic illustration showing a left side elevational view of the pump of FIG. 13.

FIG. 5 presents a flow diagram illustrating another exemplary method of operation 500 for the architecture according to FIG. 1, relating to the transmission of a message from the access point 40 to be received by one of the medical devices 10. This enables the access point 40, for example, to communicate with medical devices in order to download new firmware or software, to respond to error messages initiated by the medical devices (for example, to re-set a device or remove it from service, or to run device diagnostics), and to operate the medical device (for example, to adjust a flow rate on a feeding pump).

At step 502 of the method 500, the message is received at the first one of the relay modules 30a from the access point 40 via the WWAN. At step 504, the one relay module 30 determines whether the message is intended to reach one of the interface circuits 15 and/or other relay modules 30, 30a located in the facility 20. This may be accomplished, for example, by maintaining a list of active devices 15 and modules 30, 30a in the buffer 35 or in a manner otherwise accessible to the one relay module 30a, or coding an identifier of the interface circuit 15 or module 30, 30a to include an identity of the facility 20 that is stored in the buffer 35 or is otherwise identifiable to the one relay module 30. In the alternative, the received message may include a device identifier such as a serial number or an assigned identifier. Such a received message would then be broadcasted to all or a subset of interface circuits 15 in the facility and each interface circuit 15 determines if it was the intended recipient or should otherwise act upon or ignore the message.

If the one relay module 30a determines at step 506 that the interface circuit 15 or module 30, 30a is not located in the facility, the one relay module 30 may preferably proceed to discard the message at step 508, and/or alternatively alert the access point 40 with a non-delivery message. If the interface circuit 15 is located in the facility 20, the one relay modular 30 determines at step 510 whether the interface circuit 15 or relay module 30, 30a accessible to the one relay device 30 via the WLAN or WPAN (for example, by consulting a list stored in the buffer 35 or that is otherwise accessible to the one relay module 30, or by instructing the transceiver 31 to send a handshake or test transmission directed to the interface circuit 15 and to listen for a reply).

If the one relay module 30a determines at step 512 that the device 15 or relay module 30, 30a is accessible, then at step 514, it transmits the message via network 16 to that device or relay module via the transceiver 31. If the one relay module 30a alternatively determines at step 512 that the device or relay module is not accessible, it proceeds at step 516 to determine whether a second relay module 30, 30a is accessible via the WLAN or WPAN (for example, by instructing the transceiver 31 to send a handshake or test transmission directed to the second relay module and to listen for a reply). If the second relay module 30, 30*a* is available, then the one relay module 30 forwards the message to the transceiver 31 for transmission to the second relay module 30, 30*a* over the WLAN or WPAN. If the second relay module 30, 30*a* is inaccessible, then this portion of the process 500 may preferably be repeated to search for a third relay module 30, 30*a* that is accessible. Alternatively, or in the event that no other relay module 30, 30*a* is available, the one relay module 30 may preferably issue an alarm notification at step 522, preferably in one of the same manners described above in reference to the method 400 of FIG. 4.

The novel architecture disclosed herein for providing networked communications between a series of medical devices and a remote monitoring device provides a number of distinct advantages in comparison to other monitoring systems. By employing ZIGBEE networks based on the IEEE 802.15.4 standard according to a preferred embodiment for wireless communications between the medical devices 10 and relay modules 30, 30*a*, power and size requirements can be minimized so that the interface circuits 15 can be easily and inexpensively applied to and/or integrated with the medical devices 10.

By introducing relay modules 30*a* that are part of the ZIGBEE networks and are directly able to access off-site monitoring devices via a WWAN, access to and reliance on existing and potentially unreliable LAN facilities at a facility can be avoided. By incorporating relay features into the relay modules 30*a* that relay communications from a first relay module 30*a* to a second relay module 30*a* in the event that WWAN access to the first relay module 30*a* has been compromised, the present invention improves reliability and enables the use of conventional, low-cost cellular transceivers in the relay modules 30*a* for accessing the WWAN.

By limiting the configuration of cellular transceivers to just the relay modules 30*a*, costs can be further reduced. In addition, providing the relay modules 30*a* in a compact enclosure facilitates the relay modules 30*a* to be easily connected to reliable commercial power sources and easily moved when needed to reconfigure the ZIGBEE networks according to facilities changes.

It should of course, be understood that while the present invention has been described with respect to disclosed embodiments, numerous variations are possible without departing from the spirit and scope of the present invention as defined in the claims. For example, the present invention may be based on any of a number of current and future WPAN, WLAN and WWAN standards beyond those explicitly described herein. It should also be understood that it is possible to use exclusively relay modules 30 in the WLAN or WPAN network 16 of FIGS. 1 and 2, with transceivers for communicating with other relay modules as well as over the WWAN.

In addition, respective interface circuits useable with the present invention may include components of and perform the functions of the module 30 to provide greater flexibility in accordance with the present invention. Further, numerous configurations of components for relay module 30 are useable with the present invention beyond the components shown in FIG. 3. For instance, an input-output buffer may be used with respective switches under control of a processor for directing medical device data to transceivers 31, 32 as needed. Moreover, it is intended that the scope of the present invention include all other foreseeable equivalents to the elements and structures as described herein and with reference to the drawing figures. Accordingly, the invention is to be limited only by the scope of the claims and their equivalents. It should be appreciated that reference is sometimes made herein to a docking station configured for use with an enteral feeding pump. After reading the description provided herein, however, those of ordinary skill in the art will appreciate that the concepts and techniques described herein may be used in a wide variety of systems comprising docking stations and other types of pumps or other types of medical devices.

Figure 20:
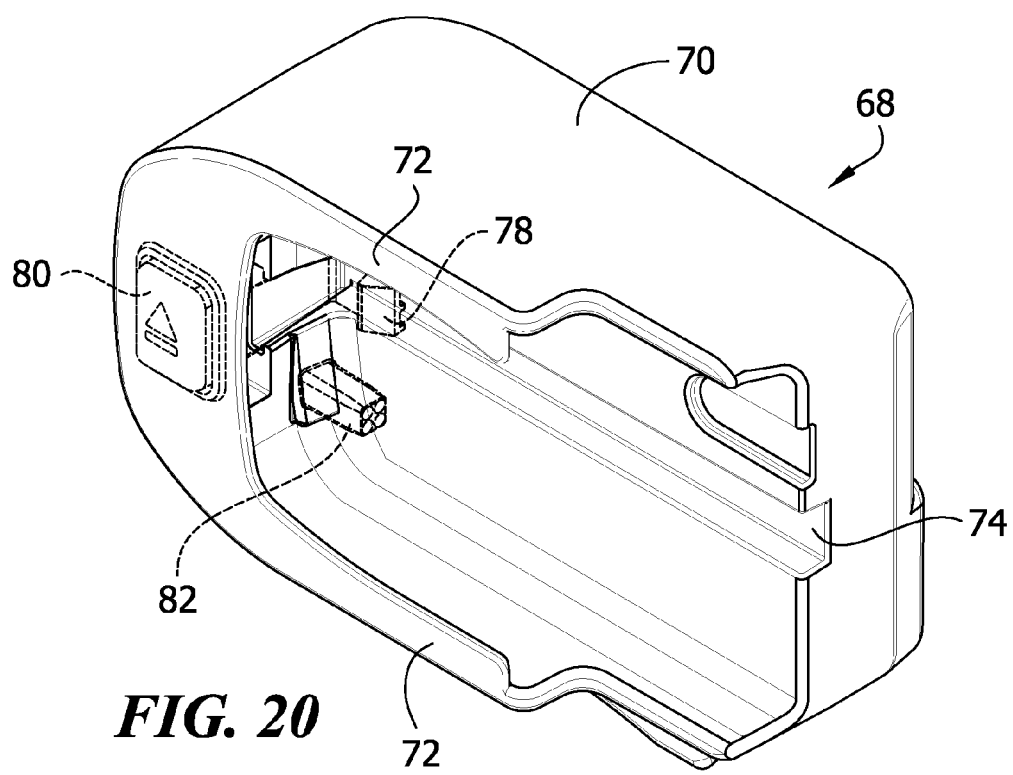
FIG. 20 is a schematic illustration showing a front perspective view of the docking station (without the pump) of FIG. 6.
Figure 21:
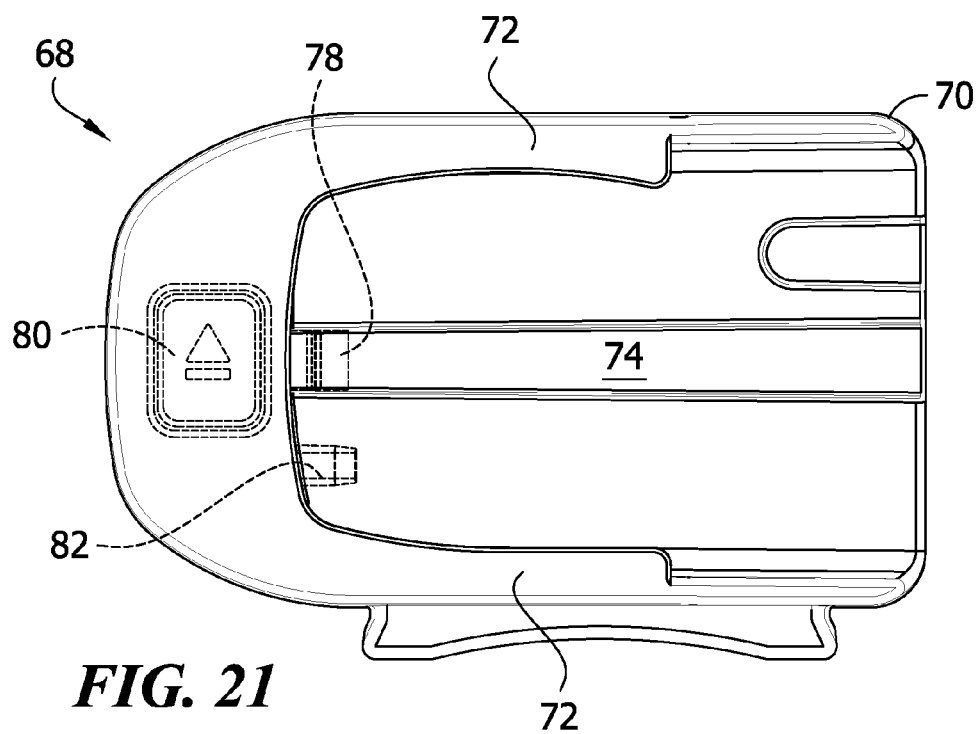
FIG. 21 is a schematic illustration showing a front elevational view of the docking station of FIG. 20.
Figure 22:
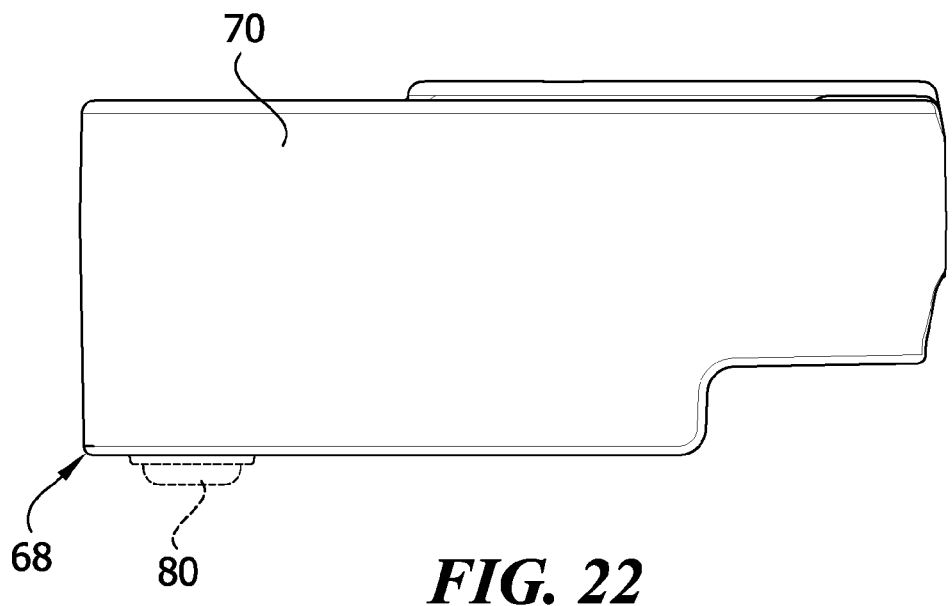
FIG. 22 is a schematic illustration showing a top plan view of the docking station of FIG. 20.
Figure 23:
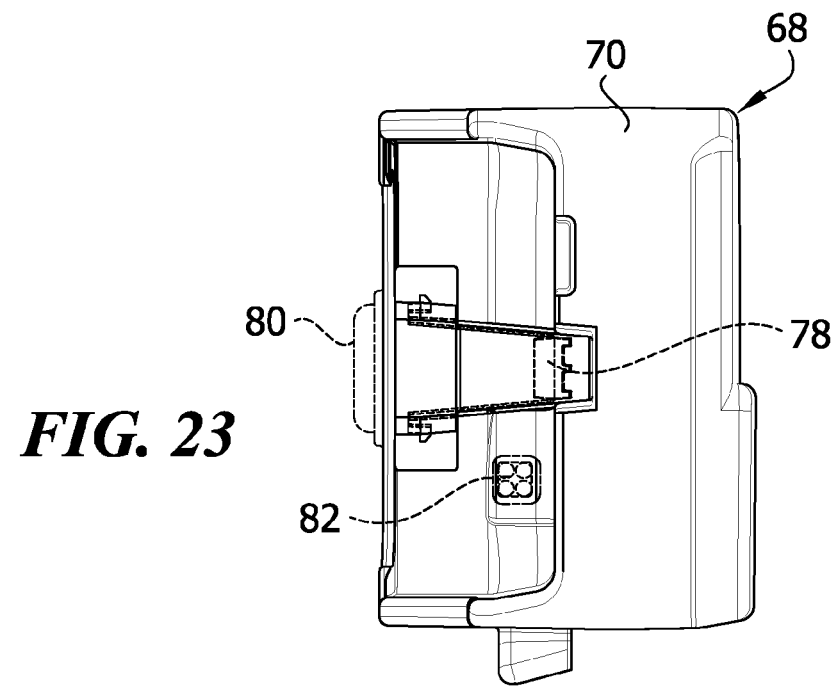
FIG. 23 is a schematic illustration showing a right side elevational view of the docking station of FIG. 20.
Figure 24:
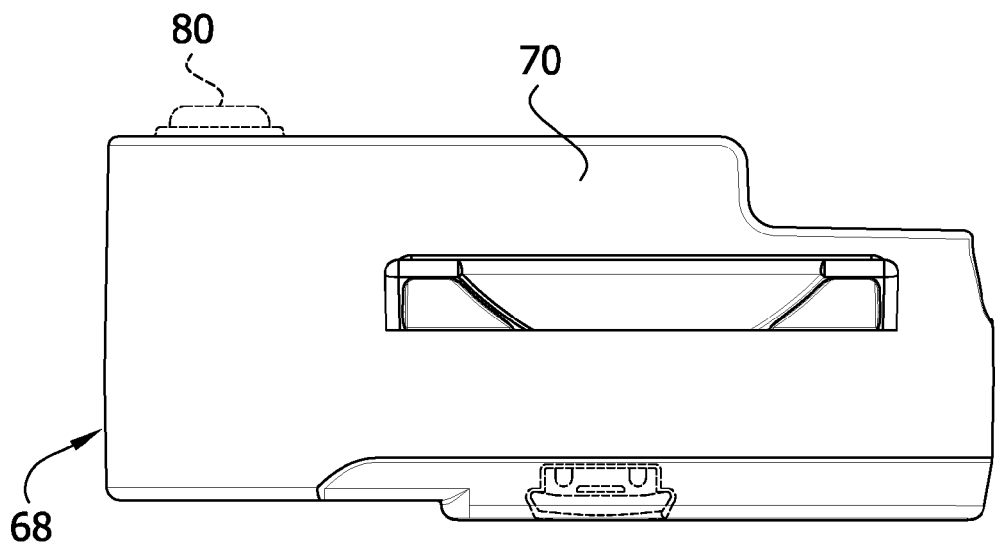
FIG. 24 is a schematic illustration showing a bottom plan view of the docking station of FIG. 20.
Figure 25:
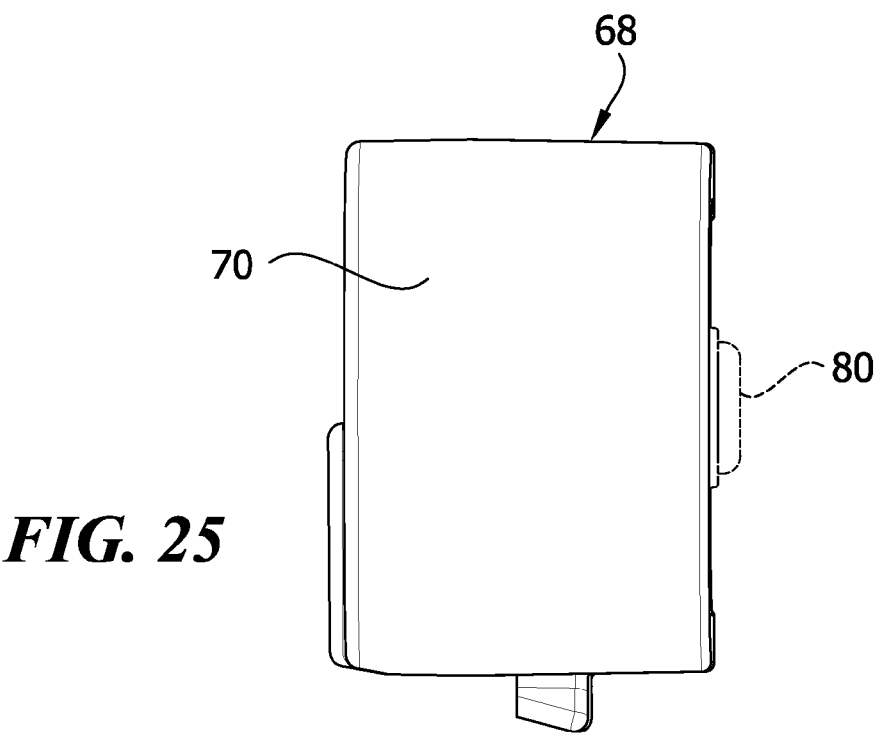
FIG. 25 is a schematic illustration showing a left side elevational view of the docking station of FIG. 20.

The system can include an enteral feeding pump coupled to a docking station. The docking station receives information provided thereto from the feeding pump and wirelessly communicates such information to a remote system (e.g. a remote monitor). Referring now to FIGS. 6-25, a docking station 68 as a relay module 30, which can be adapted for use with an enteral feeding pump as a medical device 10, includes a base portion 70 and side walls 72 projecting from the base portion. The base portion 70 has a surface configured to accept the enteral feeding pump 10. The side walls 72 form guide rails which serve to aid in aligning and guiding the enteral feeding pump 10 into a desired position on the base portion 70. Base portion 70 has a channel 74 (FIG. 20) which also serves to aid in aligning and guiding the enteral feeding pump 10 into a desired position on the base portion 70. The length, width, depth and shape of the channel 74 are selected to accommodate a corresponding boss or flange (not shown) on the enteral feeding pump 10 to be docked in the docking station 68.

The docking unit or station 68 can further include a latch 78 configured to engage or mate with a corresponding catch on the enteral feeding pump. When the feeding pump 10 is appropriately engaged on the base surface, the latch 78 facilitates securing the enteral feeding pump to the docking station 68. A release mechanism 80 such as a push-button type release mechanism can be utilized and configured to release the enteral feeding pump.

The docking station 68 further typically includes a communication/power port 82 (broadly, "a docking port"). The communication/power port is here shown projecting from a surface of the docking station sidewall. Those of ordinary skill in the art will appreciate, of course, that the communication/power port may be disposed on either of base or side surfaces. The specific location of the communication/power port in any particular application is selected may be based upon the location of the mating port 84 on the enteral feeding pump 10 to be docked in the docking station 68. Thus the specific location and configuration of the communication/power port 82 is selected such that it can coupled to a mating port 84 provided on the enteral feeding pump 10. It should also be appreciated that two separate ports may also be used (e.g. one port for communication and a separate port for power) depending, at least in part upon the requirements of the pump to be mated to the docking station.

The docking station 68 further includes a communication module (for example transceivers 31, 32 of relay module 30*a*) configured to communicate with the enteral feeding pump. The communication module may include a transceiver to transmit and receive signals. The docking station further includes a charging module (for example power supply 37, 38, 39 of relay module 30*a*) which provides power to the enteral feeding pump (e.g. to charge a power source within the enteral feeding pump). The docking station charging and communication modules may be coupled to the communication/power port 82 and communicate to the pump 10 via the communication/power port (i.e. a physical or hardwire connection). It should also be appreciated that in preferred embodiments, the communication module is provided as a wireless communication module which allows the docking station 68 to communicate wirelessly with the pump 10. Similarly, it should be appreciated that in some embodiments, the charging module (and in particular a portion of power supply circuit 37) may be provided as a wireless charging module (e.g. using electromagnetic coupling) which allows the docking station 68 to wirelessly charge a power source (e.g. one or more rechargeable batteries) in the pump 10.

Regardless of whether the communication module communicates wirelessly with the pump 10, the docking station communication module allows the enteral feeding pump to communicate with one or all of: a local hospital network; an intranet; an internet; and/or a remote device or system. In one embodiment, the docking station 68 receives data and information from the pump 10 and wirelessly communicates such data and information to nurses, health care providers and healthcare equipment companies via one or more network communication links. In further embodiments, the docking station 68 facilitates transfer of data, information, and instructions from one or more remote devices (not shown) to the medical device such as the feeding pump 10. For example, the docking station 68 can comprise a receiver or a transceiver (such as those described in relay module 30a) configured to receive instructions from a remote server over a wireless communication network such as any of a cellular or mobile network utilizing any of the GSM, GPRS, CDMA, EV-DO, EDGE, 3GSM, DECT, TDMA, iDE protocols. In other cases, the receiver or transceiver is configured to transfer instructions through a wireless local area network utilizing one or more IEEE 802.11 protocols.

Any of portion of the data, instructions, and information received and/or transmitted can be encrypted utilizing any suitable protocol such as those based on WEP and WPA.

In one embodiment, the docking station 68 further includes a WIFI/cellular wireless board such as relay module 30) inside the base portion 70. By disposing the WIFI/cellular wireless board inside the base portion (as opposed to having the WIFI/cellular wireless board internal to the enteral pump), the enteral feeding pump 10 remains relatively small and light (and thus ambulatory) while still providing wireless communication capability. Thus a combination wireless docking station and enteral feeding pump combination is provided in which the size and weight of the enteral feeding pump is such that the enteral feeding pump remains ambulatory while still providing wireless communication capability. The base portion 70 includes an antenna coupled to the communication module to aid with transmission and/or reception of signals provided from/to the docking station via the communication module.

In one embodiment, the wireless module is integral to the base portion 70. This provides a user benefit because by making the wireless module integral to the base portion (which also charges the enteral feeding pump 10) it will be difficult to lose the wireless module. This is particularly true since the docking station 68 (and thus base portion) will often be attached or otherwise coupled, to an IV pole.

In some embodiments, the base portion 70 includes a wireless charging module located within a cavity internal to the base portion of the docking station. In one embodiment, the base portion 70 is provided having a size, shape and configuration which allows the docking station 68 to be disposed on a tabletop.

In some embodiments, the base portion 70 includes a support device (e.g. a clamp member 90) which allows the docking station to be clamped to another object such as an IV pole or some other mobile support unit (e.g. a wheelchair).

In some embodiments, the docking station 68 further comprises means for quick disconnection from the IV pole for ambulatory use. In ambulatory cases, it may be beneficial to have the pump provide power to the wireless module via the communication/power port 82 when AC power is not available. This is a great advantage in that it provides freedom and mobility to the wireless module allowing wireless access with the patient is going about daily activities where direct AC power is configured to couple to an enteral feeding pump or other medical device.

As discussed above, in preferred embodiments, the docking station 68 includes a wireless transmitter for communicating data, such as operating parameters and/or status, to a remote monitor over a wireless communication link, to permit remote monitoring of certain pump diagnostics. In some embodiments, the docking station 68 may utilize the wireless communication link to permit control and/or data exchange with the feeding pump 10. This may be in addition to or in place of the remote monitoring. The pump may also contain a receiver for receiving data such as operating parameter instructions, general operating instructions, and/or commands.

The wireless communication link may be provided utilizing cellular telephony technology. In other embodiments other wireless communication technologies may be used including, but not limited to any wireless technology based, in whole or in part, upon the IEEE 802.11 standards. For example, WiFi technology, Blue Tooth technology, ZigBee technology may be used.

Thus, the docking station 68 allows an enteral feeding pump 10 to communicate wirelessly with and to dock to a charging base which, in turn, communicates with one or all of: a local hospital network; an intranet; an internet; and/or a remote device or system. In one embodiment, the docking station 68 communicates data and information to nurses, health care providers and healthcare equipment companies via one or more network communication links.

In general overview, the docking station 68 described herein includes a charging base having the necessary electrical circuitry and mechanical structures to perform a charging function as well as: (1) providing a direct physical linkage or docking of the pump 10 with the wireless module charging base; (2) during this direct linkage, the charging base provides power to the pump to ensure that rechargeable power sources 92 (e.g. rechargeable batteries) on the pump receive charging while attached to the charging base; (3) the charging base will have a quick disconnect pole clamp member 90 that allows the charging base to be attached to the IV pole and then easily removed via quick disconnect so the wireless module can be used ambulatory with the pump. This would leave a portion of the pole clamp still affixed to the IV pole. This also allows for easy reconnection to the IV pole after ambulatory use; (4) the charging base can have the alternate ability to receive power for wireless communication via the direct link to the pump in an ambulatory situation. In this condition, the backup battery 92 on the pump 10 could provide sufficient power to send wireless signals when no AC power is available; (5) it is further possible that the charging base would contain its own rechargeable battery in the event that the charging base moves with the pump in an ambulatory/backpack situation; (6) In similar fashion to 4, the pump could receive extra battery life using the battery in the charging base; (7) the base module will have the capability to sit on a tabletop or be clamped to an IV pole.

A docking station 68 as described herein allows the size and weight of an enteral feeding pump to remain small and ambulatory while still providing wireless communication capability. This is due to the storage of one or more WIFI/cellular wireless boards (such as relay module 30) inside the charging base as opposed to having the WIFI/cellular wireless board internal to the pump 10.

The base module will charge the battery in the pump 10, The base module includes means for mounting to an IV pole. The base module allows for quick disconnection from the IV pole for ambulatory use. In ambulatory cases, it may be beneficial to have the pump provide power to the wireless module via the communication/power port 82 when AC power is not available. This is a great advantage in that it provides freedom and mobility to the wireless module allowing wireless access with the patient is going about daily activities where direct AC power is impractical. Including a battery with the charging base also provides the benefit of providing wireless communication directly from the base in ambulatory situations, but also, could possibly provide additional battery life to the pump while it maintains its direct power linkage to the pump.

Referring in particular to FIGS. 6-12, the docking station 68 is exemplarily shown with the enteral feeding pump 10 coupled thereto. As most clearly visible in FIGS. 6-9, the pump 10 is securely held in the docking station. In this position, the charging module charges one or more power sources within the pump 10 and the communication module communicates with the pump by providing, for example, direct current at any suitable or desired voltage potential, e.g., any of 5 volts and 12 volts, at any suitable or desired current. The charging module can further comprise any of an inverter and charge state circuitry.

A power cord (not shown) with a first end (or plug end) is connectable, or is otherwise coupled, to a socket (or power port) provided on a back surface of the base portion of the docking station. A second end of the power cord leads to a wall adapter which allows the docking station to receive power from a standard wall outlet (e.g. North American standard of 120 volts at a frequency of 60 Hz, or European standard of 220-240 volts at 50 Hz).

As discussed above, the docking station communication module allows the enteral feeding pump to communicate wirelessly with one or all of: a local hospital network; an intranet; an internet; and/or a remote device or system. In one embodiment, the docking station communicates data and information to nurses, health care providers and healthcare equipment companies via one or more network communication links.

Such communication may be accomplished via a WIFI or cellular service. Since the WIFI/cellular communication module is disposed as part of the docking station, (as opposed to having the WIFI/cellular wireless board internal to the enteral pump), the enteral feeding pump remains relatively small and light (and thus ambulatory) while still providing wireless communication capability. Thus, a wireless docking station and enteral feeding pump combination is provided in which the size and weight of the enteral feeding pump is such that the enteral feeding pump remains ambulatory while still providing wireless communication capability via the docking station.

In one embodiment, the docking station includes a wireless transmitter for communicating data, such as operating parameters and/or status, to a remote monitor over a wireless communication link, to permit remote monitoring of certain pump diagnostics. In some embodiments, the docking station may utilize the wireless communication link to permit control and/or data exchange with the feeding pump. This may be in addition to or in place of the remote monitoring. The pump may also contain a receiver for receiving data such as operating parameter instructions, general operating instructions, and/or commands.

In one embodiment, the feeding pump may also contain a wireless transmitter for communicating data, such as operating parameters and/or status, to a remote monitor over a wireless communication link, preferably utilizing cellular telephony technology to permit remote monitoring of certain pump diagnostics. The feeding pump may also contain a receiver for receiving data such as operating parameter instructions, general operating instructions, and/or commands.

The docking station typically includes electrical contacts through which power and communication signals may be coupled between the feeding pump and docking station.

A detachable clamp can be coupled to the docking station 68 via the clamp member 90. The clamp is suitable for mounting or otherwise coupling the docking station (with pump in or out) to an IV pole or other support structure. Preferably, the docking station 68 and pump 10 are coupled to a mobile support structure thereby allowing the system to be ambulatory.

Either or both of the docking station and pump may have a communications module provided as part thereof.

Power may be supplied the docking station via a removable plug and wall adapter. The plug/wall adapter can be coupled directly to the docking station or directly to the pump.

In further embodiments, the system can be implemented as a home care ambulatory enteral feeding pump includes a communication module capable of communicating within a personal area network (PAN). In those embodiments in which the feeding pump is provided with only a ZigBee communication set (or similar), the feeding pump cannot communicate via cellular technology.

The systems, circuits and techniques described herein are not limited to the specific embodiments described. Elements of different embodiments described herein may be combined to form other embodiments not specifically set forth above. Other embodiments not specifically described herein are also within the scope of the following claims.

The invention claimed is:

1. A docking station for an enteral feeding pump, the docking station comprising:
    a base portion configured to hold the enteral feeding pump, the base portion including a channel to align the enteral feeding pump;
    a docking port disposed on the base portion and configured to couple to a mating port provided on the enteral feeding pump;
    a wireless communication module configured to communicate with the enteral feeding pump, the communication module includes a transceiver to transmit and receive signals permitting the enteral feeding pump to wirelessly communicate with at least one of a local hospital network, an intranet, and a remote device; and
    a charging module located within a cavity internal to the base portion, the charging module providing power to the enteral feeding pump when the pump is docked in the docking station.

2. The docking station of claim 1 wherein the charging module is provided as a wireless charging module which allows the docking station to wirelessly charge a power source in the pump.

3. The docking station of claim 1 wherein the base portion is provided having a size, shape and configuration which allows the docking station to be disposed on a tabletop.

4. The docking station of claim 1 further comprising one or more of a WIFI and a cellular wireless board disposed internal to the base portion.

5. The docking station of claim 1 wherein the wireless communication module is integral to the base portion.

6. The docking station of claim 1 further comprising a clamp member coupled to the docking station, the clamp member being suitable for mounting or otherwise coupling the docking station to an IV pole or other support structure.

7. The docking station of claim 1 further comprising a rechargeable battery disposed in the base portion to provide extra battery life to the enteral feeding pump in the event that the docking station moves with the pump in an ambulatory/backpack situation.

8. A system comprising an enteral feeding pump and a docking station, the docking station comprising:
   a base portion configured to hold the enteral feeding pump, the base portion including a channel to align the enteral feeding pump;
   a docking port disposed on the base portion and configured to couple to a mating port provided on the enteral feeding pump;
   a wireless communication module configured to communicate with the enteral feeding pump, the communication module includes a transceiver to transmit and receive signals permitting the enteral feeding pump to wirelessly communicate with at least one of a local hospital network, an intranet, and a remote device; and
   a charging module located within a cavity internal to the base portion, the charging module providing power to the enteral feeding pump when the pump is docked in the docking station.

9. The system of claim 8 wherein the enteral feeding pump comprises one or more rechargeable batteries and wherein in response to the enteral feeding pump being attached to the base portion, the charging module is placed in electrical communication with the one or more rechargeable batteries in the enteral feeding pump to charge the pump.

10. The system of claim 8 wherein the docking station includes a clamp member, the clamp member being suitable for mounting or otherwise coupling the docking station to an IV pole or other support structure.

11. The system of claim 8 wherein the enteral feeding pump includes a power source operatively coupled to provide power to the wireless communication module.

12. The system of claim 8 wherein the enteral feeding pump includes a power source operatively coupled to provide power to the charging module via the docking port when AC power is not available.

13. The docking station of claim 8 wherein the enteral feeding pump includes a backup battery to provide power to send wireless signals when no AC power is available.

* * * * *